United States Patent
Jacobs

(10) Patent No.: US 9,622,695 B2
(45) Date of Patent: Apr. 18, 2017

(54) VACUUM ASSISTED LANCING SYSTEM AND METHOD FOR BLOOD EXTRACTION WITH MINIMAL PAIN

(71) Applicant: Christopher A. Jacobs, Midland, TX (US)

(72) Inventor: Christopher A. Jacobs, Midland, TX (US)

( * ) Notice: Subject to any disclaimer, the term of this patent is extended or adjusted under 35 U.S.C. 154(b) by 531 days.

(21) Appl. No.: 13/900,872

(22) Filed: May 23, 2013

(65) Prior Publication Data
US 2013/0261500 A1 Oct. 3, 2013

Related U.S. Application Data

(63) Continuation of application No. 12/689,570, filed on Jan. 19, 2010, now Pat. No. 8,480,596.

(51) Int. Cl.
*A61B 5/00* (2006.01)
*A61B 5/151* (2006.01)
*A61B 5/15* (2006.01)

(52) U.S. Cl.
CPC ........ *A61B 5/15101* (2013.01); *A61B 5/1519* (2013.01); *A61B 5/150022* (2013.01); *A61B 5/150068* (2013.01); *A61B 5/150099* (2013.01); *A61B 5/15113* (2013.01); *A61B 5/15117* (2013.01); *A61B 5/150137* (2013.01); *A61B 5/150183* (2013.01); *A61B 5/15186* (2013.01);
(Continued)

(58) Field of Classification Search
CPC ... A61B 5/1411; A61B 5/151; A61B 5/15101; A61B 5/15103; A61B 5/15117; A61B 5/15186; A61B 5/150175
See application file for complete search history.

(56) References Cited

U.S. PATENT DOCUMENTS 4,653,513 A 3/1987 Dombrowski
5,320,607 A 6/1994 Ishibashi
(Continued)

FOREIGN PATENT DOCUMENTS

EP 1 219 242 7/2002
EP 1 449 479 8/2004
(Continued)

OTHER PUBLICATIONS

Schultz, O., International Search Report for International Patent Application No. PCT/US2011/020104, dated Dec. 19, 2011, European Patent Office.
(Continued)

*Primary Examiner* — Devin Henson
(74) *Attorney, Agent, or Firm* — Locke Lord LLP

(57) ABSTRACT

A lancing system can include a device body having a sealing device coupled to a lancing end, a lancing shaft slideably coupled to the lancing end, a lancing spring coupled to the lancing shaft, a release mechanism, a main shaft slideably coupled with a free end of the device body in communication with the release mechanism, a piston coupled to the main shaft, a vacuum spring coupled to the piston, and a shaft coupler having at least two separable portions for removably coupling the lancing shaft to the main shaft. The system can include a lance tool having an insertion portion and a removal portion. A method can include creating a first portion of a vacuum, lancing a surface, and creating a second portion of a vacuum.

19 Claims, 11 Drawing Sheets

(52) U.S. Cl.
CPC .... *A61B 5/15194* (2013.01); *A61B 5/150412* (2013.01); *A61B 5/150503* (2013.01); *A61B 5/150824* (2013.01); *A61B 5/1411* (2013.01); *A61B 5/151* (2013.01); *A61B 5/15019* (2013.01); *A61B 5/15103* (2013.01); *A61B 5/150175* (2013.01)

(56) References Cited

U.S. PATENT DOCUMENTS

| | | |
|---|---|---|
| 5,666,966 A | 9/1997 | Horie et al. |
| 5,873,887 A | 2/1999 | King et al. |
| 6,026,841 A | 2/2000 | Kozik |
| 6,027,459 A | 2/2000 | Shain et al. |
| 6,063,039 A | 5/2000 | Cunningham et al. |
| 6,071,249 A | 6/2000 | Cunningham et al. |
| 6,071,251 A | 6/2000 | Cunningham et al. |
| 6,093,156 A | 7/2000 | Cunningham et al. |
| 6,152,942 A | 11/2000 | Brenneman et al. |
| 6,155,992 A | 12/2000 | Henning et al. |
| 6,206,841 B1 | 3/2001 | Cunningham et al. |
| 6,261,245 B1 | 7/2001 | Kawai et al. |
| 6,283,926 B1 * | 9/2001 | Cunningham et al. ....... 600/573 |
| 6,306,104 B1 | 10/2001 | Cunningham et al. |
| 6,730,046 B1 * | 5/2004 | Hamamoto et al. .......... 600/583 |
| 6,837,858 B2 | 1/2005 | Cunningham et al. |
| 6,929,650 B2 | 8/2005 | Fukuzawa et al. |
| 7,131,984 B2 | 11/2006 | Sato et al. |
| 7,297,152 B2 | 11/2007 | Fukuzawa et al. |
| 7,494,498 B2 * | 2/2009 | Lipoma et al. ................ 606/182 |
| 7,662,111 B2 | 2/2010 | Cha et al. |
| 7,833,170 B2 | 11/2010 | Matsumoto et al. |
| 8,021,383 B2 | 9/2011 | Zhong |
| 2004/0249406 A1 | 12/2004 | Griffin et al. |
| 2004/0260326 A1 * | 12/2004 | Lipoma ................ A61B 5/1411 606/182 |
| 2007/0083131 A1 * | 4/2007 | Escutia et al. ................ 600/583 |
| 2009/0043324 A1 | 2/2009 | Paschal |
| 2009/0281459 A1 * | 11/2009 | Faulkner ............... A61B 5/1411 600/583 |
| 2009/0299224 A1 * | 12/2009 | Yoo ...................... A61B 5/1411 600/583 |
| 2009/0306696 A1 | 12/2009 | Doi |
| 2010/0121368 A1 * | 5/2010 | Kim .............................. 606/182 |

FOREIGN PATENT DOCUMENTS

| | | |
|---|---|---|
| JP | 11 206742 | 8/1999 |
| WO | 2005/013823 | 2/2005 |

OTHER PUBLICATIONS

Schultz, O., Written Opinion for International Patent Application No. PCT/US2011/020104, dated Dec. 19, 2011, European Patent Office.

\* cited by examiner

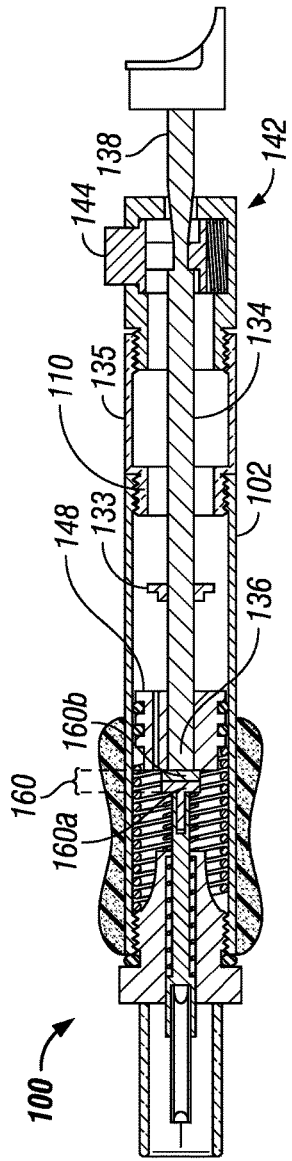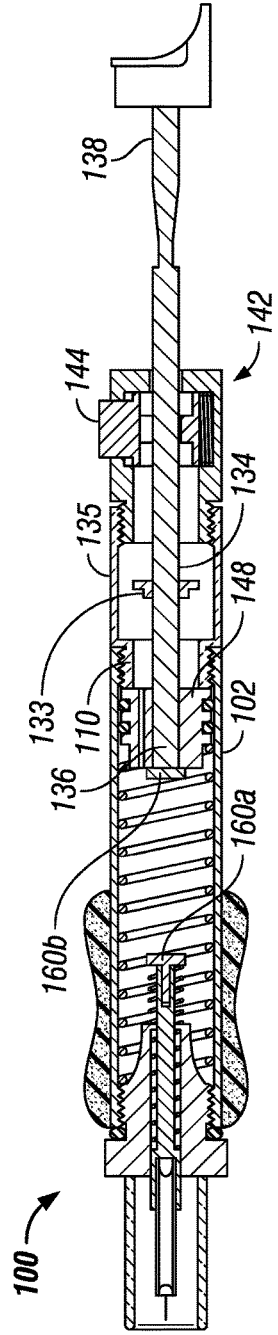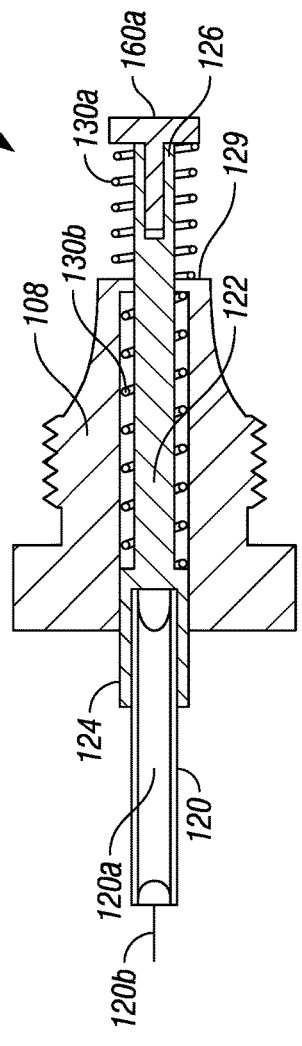
FIG. 3A
FIG. 3B
FIG. 4

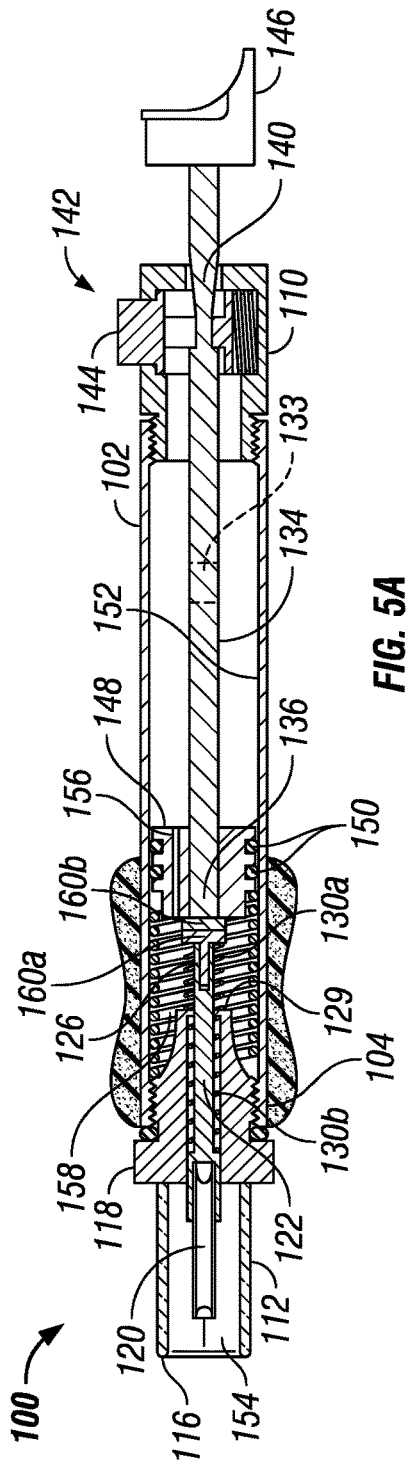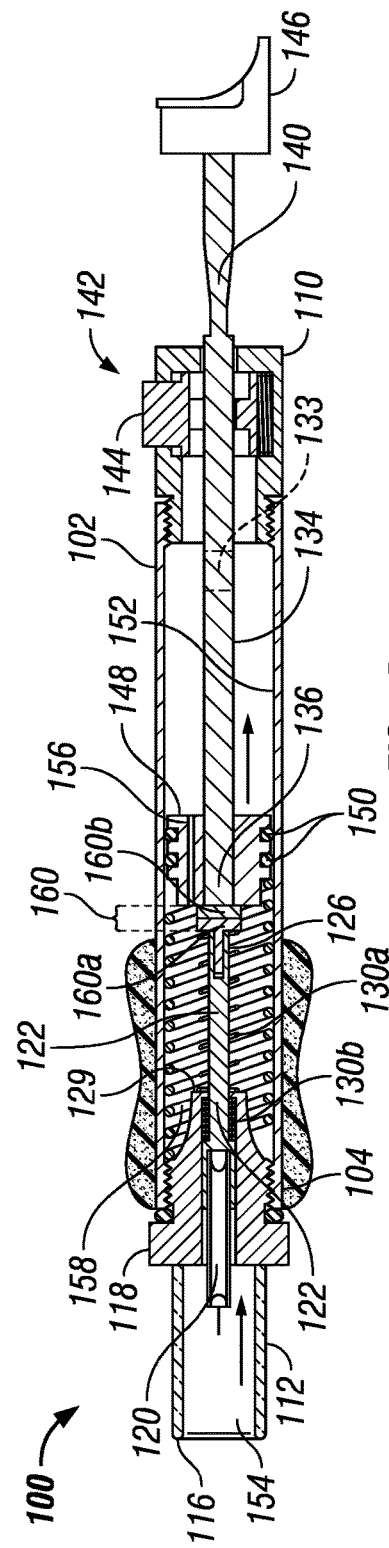

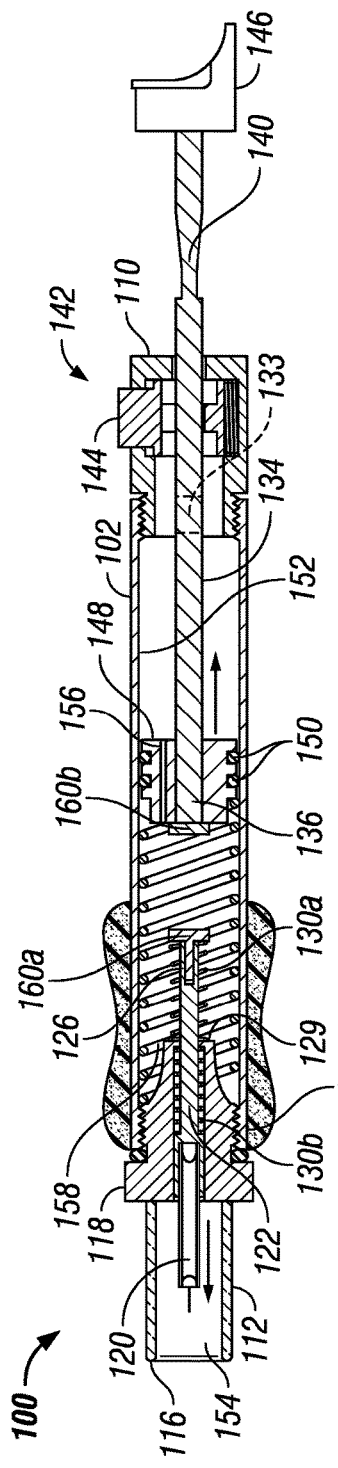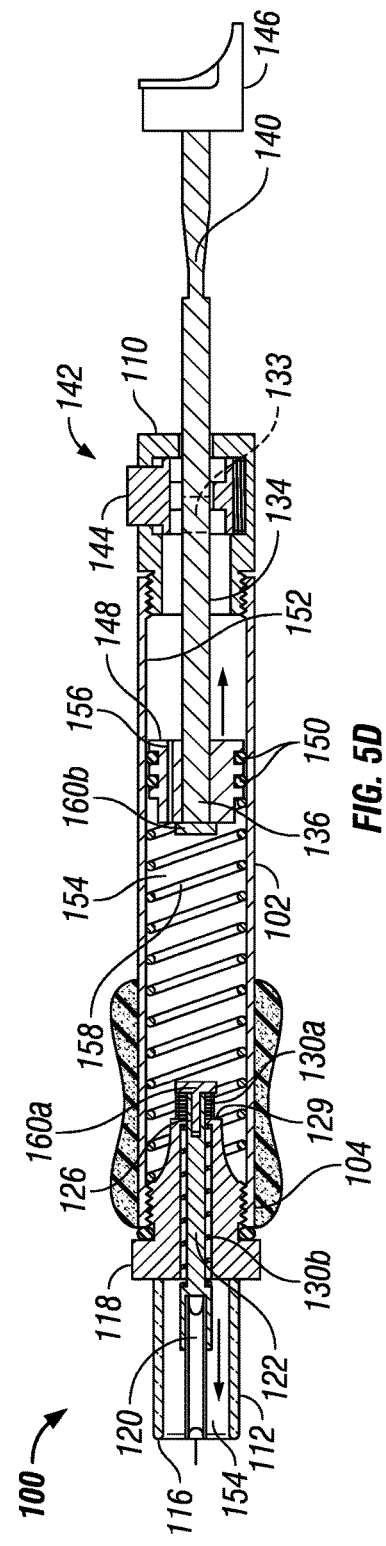

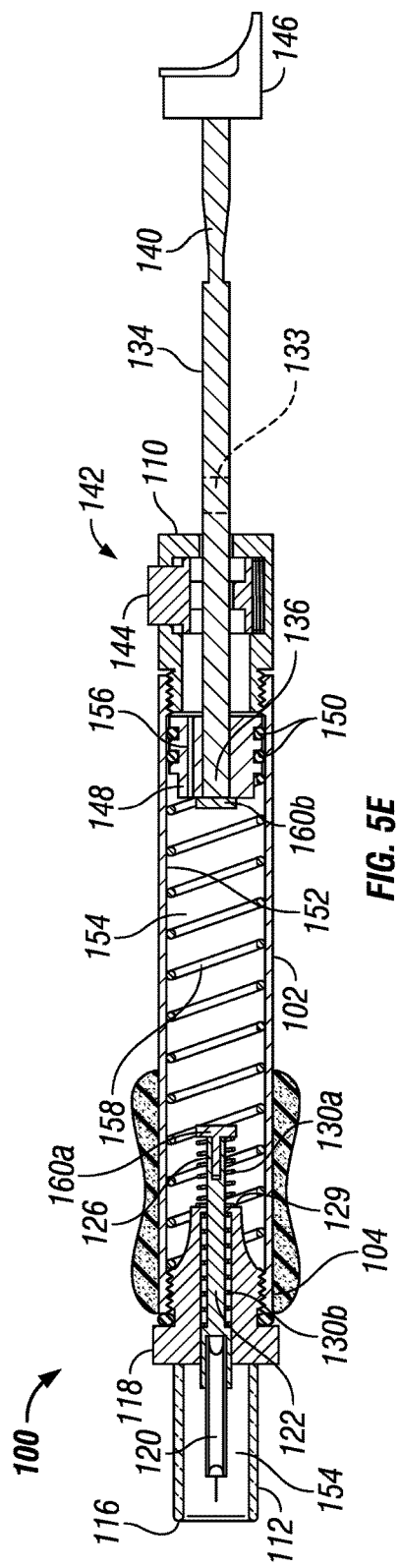
FIG. 5E
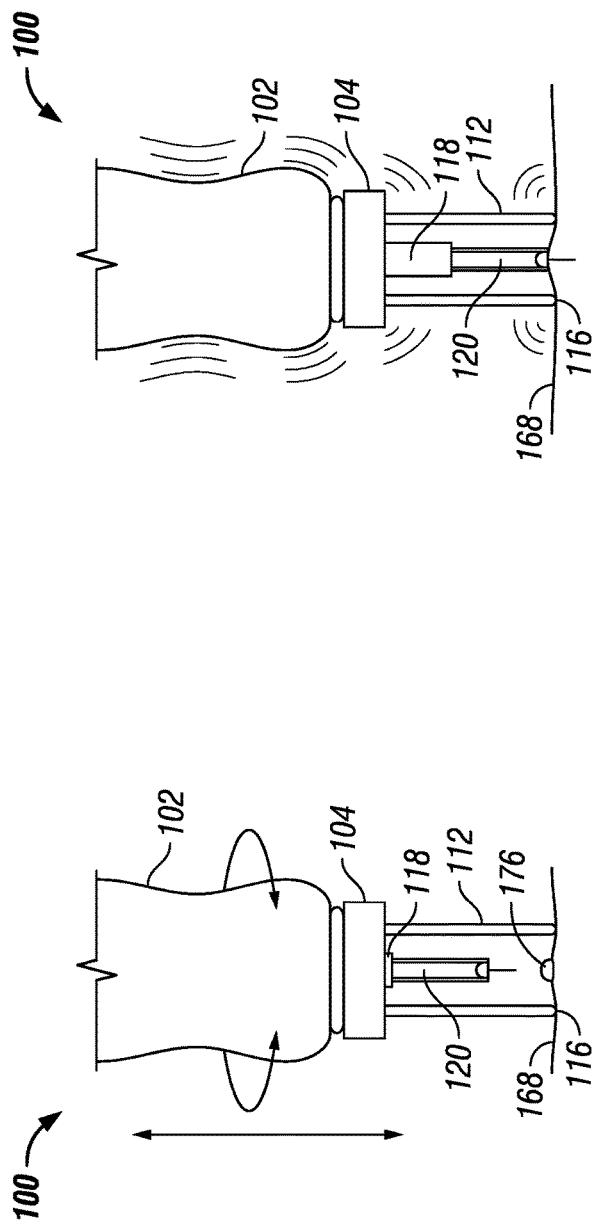
FIG. 5F
FIG. 5G

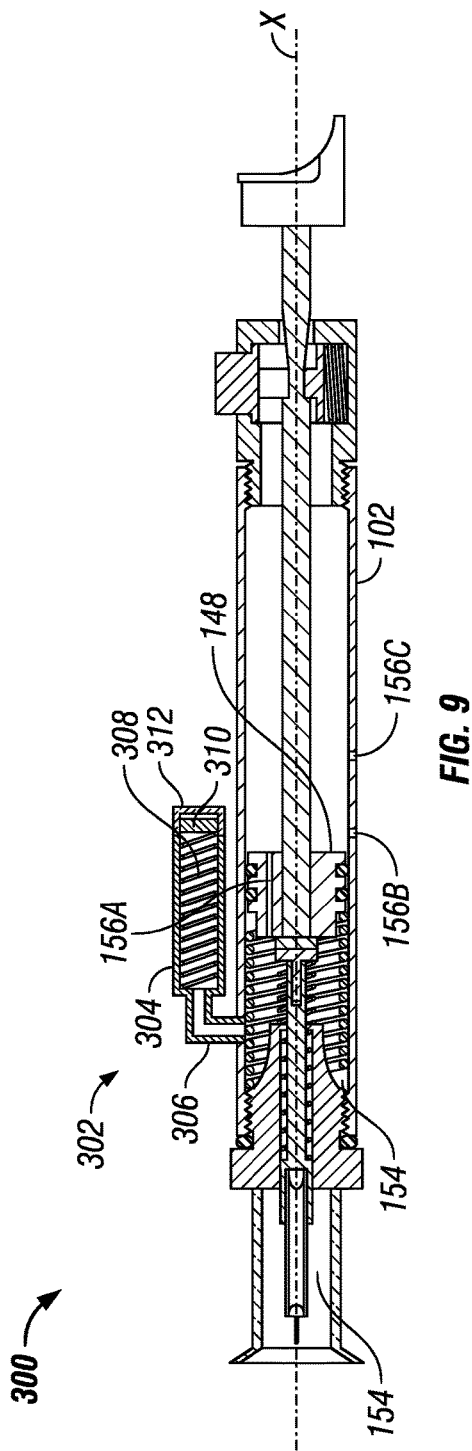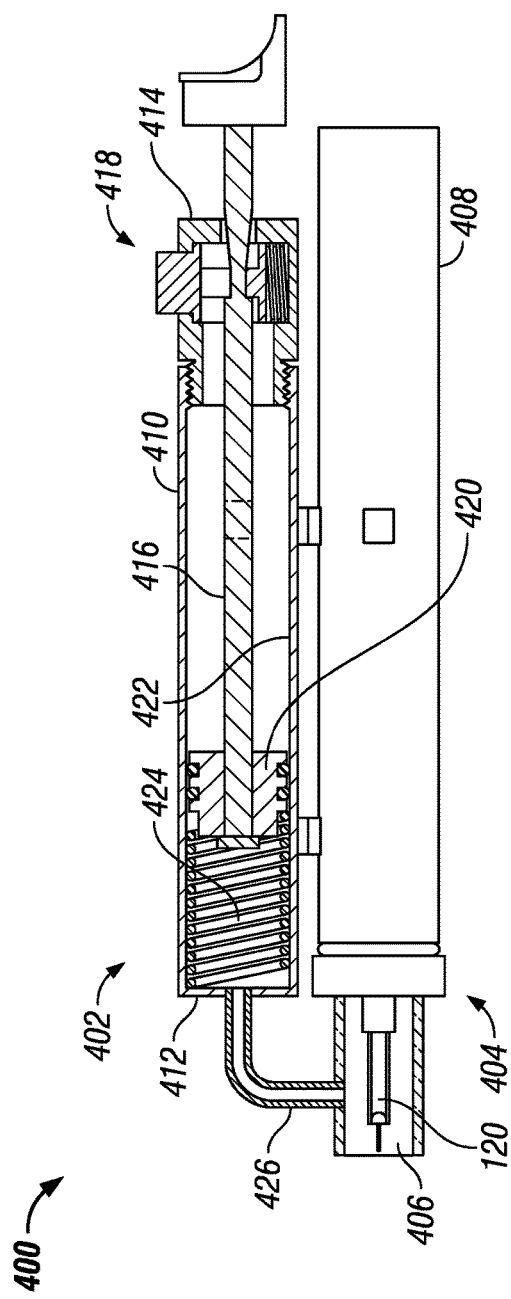

VACUUM ASSISTED LANCING SYSTEM AND METHOD FOR BLOOD EXTRACTION WITH MINIMAL PAIN

CROSS REFERENCE TO RELATED APPLICATIONS

This application is a continuation of application Ser. No. 12/689,570, filed Jan. 19, 2010. The following applications were also filed by Applicant on Jan. 19, 2010: U.S. application Ser. Nos. 12/689,608; 12/689,618; 12/689,641; 12/689,657. Applicant filed U.S. application Ser. No. 13/367,953 on Feb. 7, 2012. The entire contents of each of the foregoing applications is hereby incorporated by reference in this application.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The invention disclosed and taught herein relates generally to blood extraction devices and methods. More specifically, the invention relates to vacuum assisted lancing devices and methods useful for extracting a quantity of blood for sampling or testing.

Description of the Related Art

There are many medical reasons where a small quantity of blood needs to be drawn from a human. Determining blood glucose levels for diagnosis and treatment of diabetes is one of the most common applications where access to blood is required. Diabetes has become a significant health risk in the United States and other parts of the world. The rise in diabetes has caused alarm in the medical community. Major companies, research institutions, and the consuming public are collectively spending significant resources for the prevention, testing, and treatment of diabetes. A person with diabetes is generally required to test their blood several times a day for glucose levels and take corrective action if needed. Failure to test and take corrective action when necessary can result in injury, both long and short term degradation of the human body's functions, and in some cases death.

Currently, the market provides an assortment of devices that lance the skin producing a wound or other opening from which blood can be extracted. However, most require testing on an area of a user's skin that has a high concentration of blood vessels near the surface of the skin so that the lance can produce an acceptable quantity of blood. The most common area for testing is the finger tips, although the toes have also been used. However, these heavily vasculated areas of the human body are typically highly sensitive, having a rich supply of nerve endings. As a result, blood rich areas, such as the finger tips, often are more pain sensitive than other less vasculated areas. Thus, the very areas that are ideally suited for extracting blood for testing are the most sensitive to pain.

For those individuals who are required to test themselves, the frequent testing can have negative effects on their emotional health, physical health, and even personalities. At the least, in an effort to avoid pain, they are motivated to not test as often as required by their physician. A loss of frequency and continuity in the testing can lead to physical and emotional complications, or a significant loss of accuracy in determining proper dietary corrections and medicine regiments. Health care practitioners may also be required to lance a patient's skin to extract blood for testing, which is typically done in the fingers. In some situations, however, the fingers and toes may not be available for testing, such as when these areas of the patient's body are bandaged or injured, and an alternative testing site on the patient's body may be required.

Some blood extraction devices simply lance the skin and the patient manually squeezes the area to produce the required quantity of blood. Other blood extraction devices seek to use a vacuum to enhance the blood recovery from the lancing. However, in surveying the market of such devices, the inventor has realized that the vacuum assisted devices are either not portable with mechanized vacuum pumps, which can significantly diminish their value for mobile patients, or require unwanted maintenance, such as replacement of batteries, which are not always available. Further, many of such devices fail to adequately produce a desirable quantity of blood from portions of the skin other than the fingers and toes. Newer devices house multiple lances in the same holder, and with each use a new lance is automatically selected and used such that the patient never uses the same lance twice. Many, if not all, these devices, including the ones that apply a vacuum, have been unsuccessful in reliably extracting sufficient quantities of blood from areas of the skin less painful than the fingers and toes. Reduction or elimination of pain has been shown to appreciably encourage the patient to follow the testing procedure prescribed by an attending physician.

While each of these devices may have certain limited applications, there remains a need to provide a simplified and improved vacuum assisted lancing device that can be routinely used at various places on the skin and still extract a sufficient quantity of blood for the required test.

BRIEF SUMMARY OF THE INVENTION

A lancing system can include a device body having a sealing device coupled to a lancing end, a lancing shaft slideably coupled to the lancing end, a lancing spring coupled to the lancing shaft, a release mechanism, a main shaft slideably coupled with a free end of the device body in communication with the release mechanism, a piston coupled to the main shaft, a biasing device coupled to the piston, and a shaft coupler having at least two separable portions for removably coupling the lancing shaft to the main shaft. The system can include a lance tool having an insertion portion and a removal portion. A method can include creating a first portion of a vacuum, lancing a surface, and creating a second portion of a vacuum.

A lancing system can include a device body having a lancing end and a free end, the lancing end having a sealing device coupled thereto, a lancing shaft having a lance coupling end and an actuating end slideably coupled to the lancing end of the device body, at least one lancing spring coupled to the lancing shaft, a release mechanism, a main shaft having an actuating end and a free end slideably coupled with a free end of the device body in communication with the release mechanism, a piston coupled to the main shaft and disposed within the device body, an opening, a vacuum spring coupled to the piston so that the piston is biased toward the free end of the device body, and a shaft coupler having at least two separable portions for removably coupling the lancing shaft to the main shaft, wherein a first portion is coupled to the actuating end of the lancing shaft and a second portion is coupled to the actuating end of the main shaft.

A method of extracting blood with a vacuum assisted lancing system including a device body having a lancing end and a free end, the lancing end having a sealing device coupled thereto, a lancing shaft having a lance coupling end and an actuating end, a lance coupled to the lance coupling end of the lancing shaft, a release mechanism, a main shaft having an actuating end, a free end and a release coupler there between, wherein the main shaft is slideably coupled with the free end of the device body so that the release coupler may communicate with the release mechanism, a piston coupled to the main shaft and disposed within the device body so that a vacuum chamber is formed between the sealing device and the piston, an opening that allows fluid communication between the vacuum chamber and an atmosphere surrounding the vacuum chamber, a vacuum spring coupled within the device body so that the piston is biased toward the free end of the device body, and a shaft coupler having at least two separable portions, wherein a first portion is coupled to the actuating end of the lancing shaft and a second portion is coupled to the actuating end of the main shaft, the method including cocking the lancing system, coupling the sealing device to a surface (such as skin) for blood extraction and forming at least a partial seal between the sealing device and the surface, uncoupling the release coupler from the release mechanism, allowing the vacuum spring to at least partially deenergize, uncoupling the at least two separable portions of the shaft coupler to allow the at least two separable portions to move independently from one another within the device body, allowing the piston to travel toward the free end of such device body, creating a vacuum between the surface and the piston thereby subjecting the surface to the vacuum, and lancing the surface while the surface is subjected to the vacuum.

A lancing system for blood extraction can include a device body having a lancing end, a lancing assembly coupled at least partially inside the device body, the lancing assembly having a lance coupler portion slideably coupled with the lancing end of the device body, a lance coupled to the lance coupler portion, and a lance tool removably coupled to the lance, the lance tool including a lance insertion portion and a lance removal portion, wherein the lance insertion portion forms a clearance fit with the lance and the lance removal portion forms an interference fit with the lance, and wherein the lance insertion portion is adapted to insert the lance into the lance coupler portion so that the lance is retained in the lance coupler portion, and the lance removal portion is adapted to remove the lance from the lance coupler portion so that the lance is retained in the lance removal portion.

BRIEF DESCRIPTION OF THE SEVERAL VIEWS OF THE DRAWINGS

FIG. 3A is a cross-sectional schematic view of another of many embodiments of a vacuum lance system having an indicator according to the disclosure.

FIG. 3B is a cross-sectional schematic view of the indicator of FIG. 3A in a viewing window.

FIG. 4 is a cross-sectional schematic view of one of many embodiments of a lancing mechanism according to the disclosure.

FIG. 5A is an illustration of one of many embodiments of a vacuum lance system in a cocked position according to the disclosure.

FIGS. 5B, 5C and 5D are illustrations of the system of FIG. 5A in three respective positions during lancing.

FIG. 5E is an illustration of the system of FIG. 5A in an uncocked position.

FIG. 5F is an illustration of the system of FIG. 5A manipulating a surface during lancing.

FIG. 5G is an illustration of the system of FIG. 5A vibrating a surface during lancing.

FIG. 9 is a cross-sectional schematic view of one of many embodiments of a vacuum lance system having an external vacuum indicator according to the disclosure.

FIG. 10 is a cross-sectional schematic view of one of many embodiments of a vacuum lance system having an external vacuum assembly according to the disclosure.

DETAILED DESCRIPTION OF THE INVENTION

Figure 1:
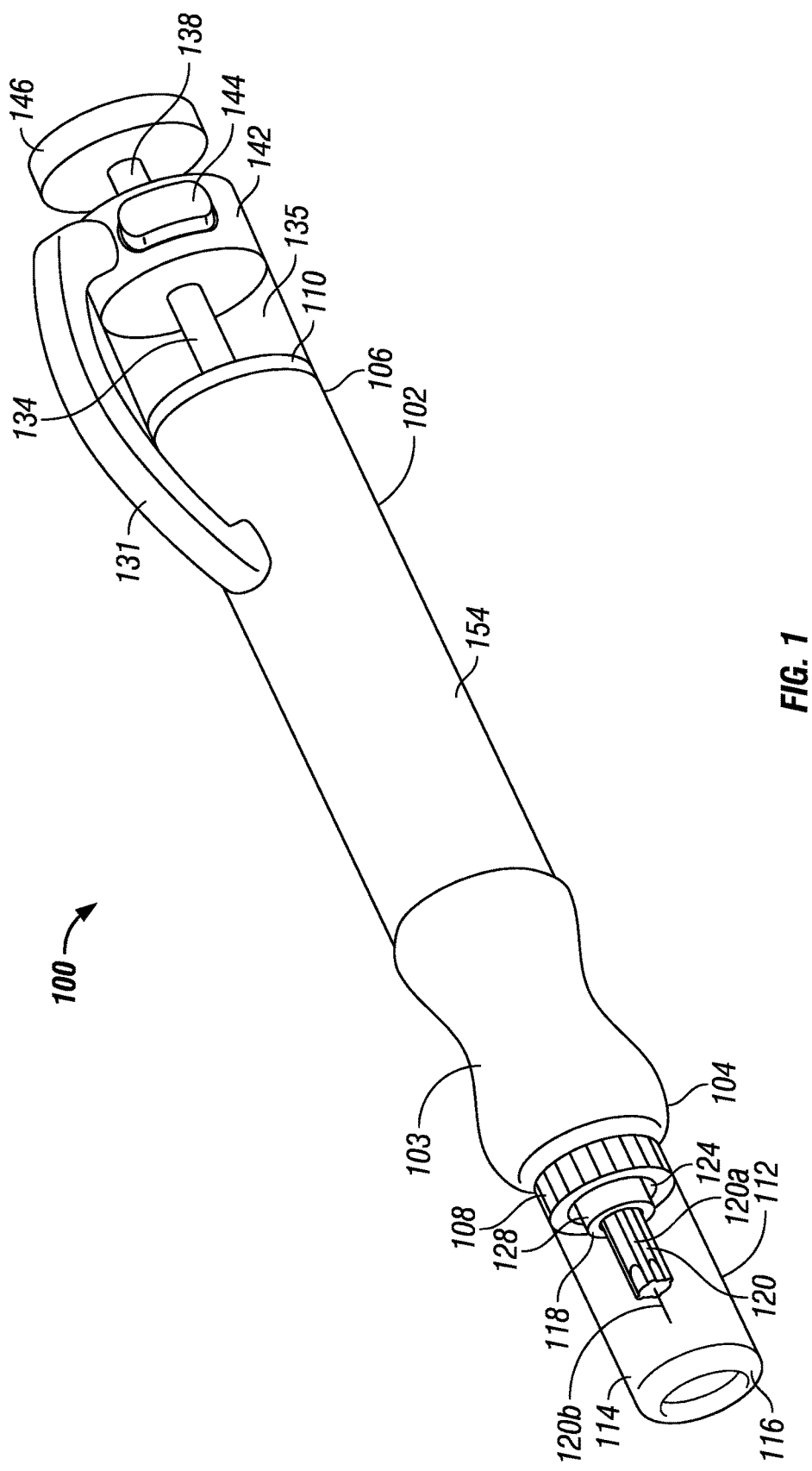
FIG. 1 is an isometric schematic view of one of many embodiments of a vacuum lance system according to the disclosure.

The Figures described above and the written description of specific structures and functions below are not presented to limit the scope of what Applicant has invented or the scope of the appended claims. Rather, the Figures and written description are provided to teach any person skilled in the art to make and use the invention for which patent protection is sought. Those skilled in the art will appreciate that not all features of a commercial embodiment of the invention are described or shown for the sake of clarity and understanding. Persons of skill in this art will also appreciate that the development of an actual commercial embodiment incorporating aspects of the present invention will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location, and from time to time. While a developer's efforts might be complex and time-consuming in an absolute sense, such efforts would be, nevertheless, a routine undertaking for those of ordinary skill in this art having benefit of this disclosure. It must be understood that the invention disclosed and taught herein is susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims. When referring generally to such elements, the number without the letter is used. Further, such designations do not limit the number of elements that can be used for that function. The terms "couple," "coupled," "coupling," "coupler," and like terms are used broadly herein and can include any method or device for securing, binding, bonding, fastening, attaching, joining, inserting therein, forming thereon or therein, communicating, or otherwise associating, for example, mechanically, magnetically, electrically, chemically, operably, directly or indirectly with intermediate elements, one or more pieces of members together and can further include without limitation integrally forming one functional member with another in a unity fashion. The coupling can occur in any direction, including rotationally.

This disclosure provides a vacuum assisted lancing system and method that can be easily used at a wide variety of places on a human or animal, even in places with less sensitivity, such as the stomach, sides, arms and legs. The system can be used with one hand and is easily portable. The system can minimize pain due to its ability to operate on unconventional areas on a user, and in at least one embodiment minimizes pain due to vibration during lancing. The term "user" and like terms are used broadly herein and include, without limitation, a person who uses the present invention on his/her self, or a person (or animal) for whom another person uses the present invention to lance the person (or animal). The system's vibration can at least partially mask any pain from a patient during lancing. Further, the lance itself can be easily replaced from a position external to the system with simple insertion. Not requiring batteries, nor containing any form of motor, the system is virtually maintenance free, other than replacement of the lance after use. The system can be easily carried to be readily available wherever the user needs to take a blood sample. Integration of this system into the common mainstream method of blood glucose measurement can be significantly assisted because the system draws from the same pool of body blood as other devices. Therefore, special glucose measuring instruments and supplies may not be required, and blood measurement procedures may not have to be altered from those currently in practice.

Figure 2:
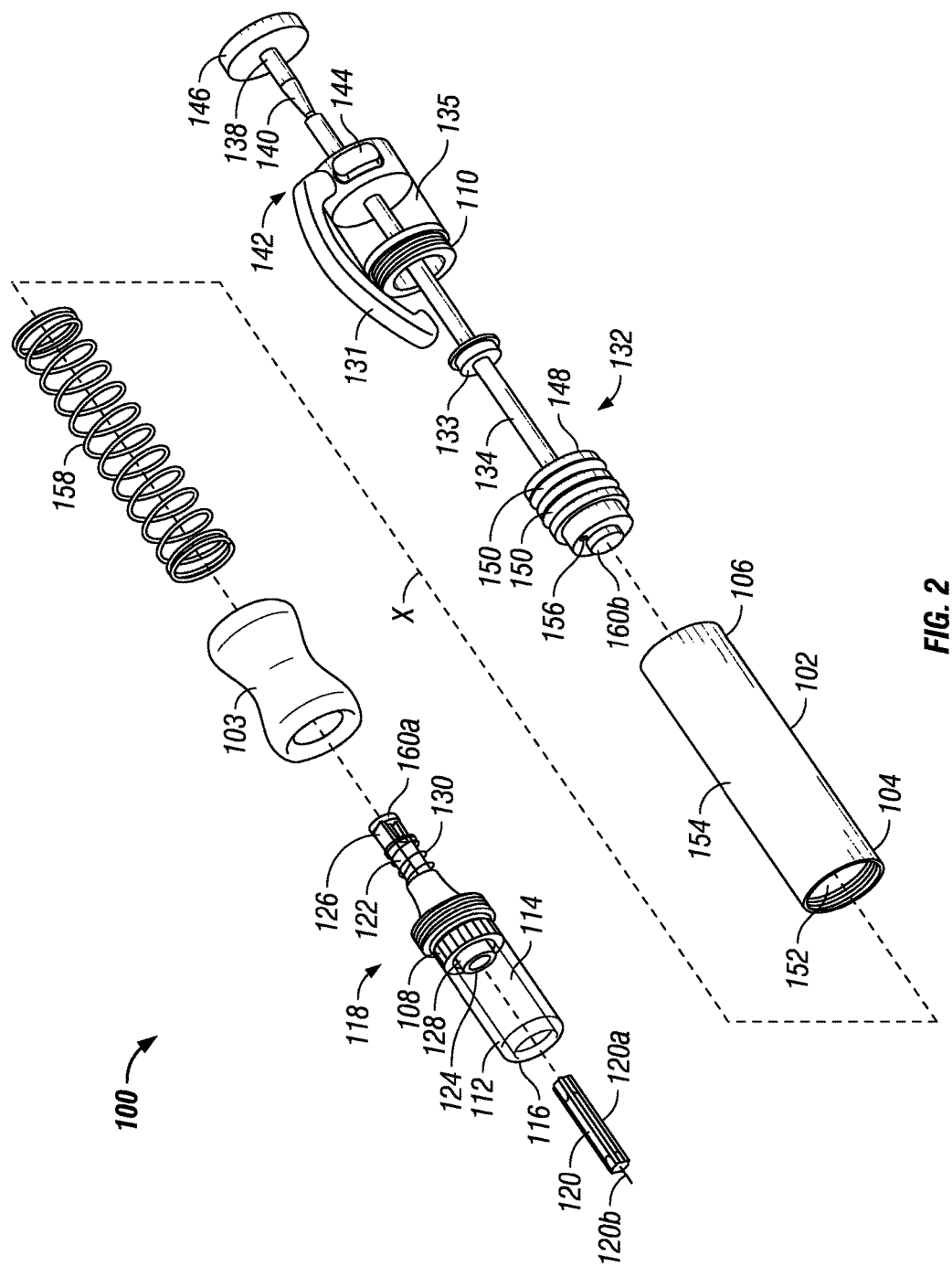
FIG. 2 is an isometric assembly schematic view of the vacuum lance system of FIG. 1.

FIG. 1 is an isometric schematic view of one of many embodiments of vacuum lance system 100 according to the disclosure. FIG. 2 is an isometric assembly schematic view of the vacuum lance system of FIG. 1. FIG. 3A is a cross-sectional schematic view of another of many embodiments of vacuum lance system 100 having an indicator 133 according to the disclosure. FIG. 3B is a cross-sectional schematic view of the indicator 133 of FIG. 3A in viewing window 135. FIG. 4 is a cross-sectional schematic view of one of many embodiments of lancing mechanism 118 according to the disclosure. FIGS. 1-4 will be described in conjunction with one another. Vacuum lance system 100 can include a device body 102, which can comprise, for example, a tubular vacuum body, for supporting one or more components for lancing. Device body 102 can have a bottom lancing end 104 and a top free end 106, and can, but need not, be transparent, in whole or in part. Device body 102 can be formed from any material, such as plastic, metal, or another material, separately or in combination, and can be any size required by a particular application. System 100 can, but need not, include a grip 103, such as a foam, rubber, plastic, or other holder, for holding the system. System 100 can, but need not, include a holder 131, such as a belt clip, pocket clip, loop, or other holder, for supporting the system, for example, when not in use.

System 100 can include one or more components for lancing (the components collectively referred to herein as a lancing assembly), which can include one or more components for vacuuming, coupled to device body 102. System 100 can include a lance guide 112, such as a tube, coupled to lancing end 104, such as for "aiming" system 100 or for contacting a lancing surface, such as skin, for lancing, directly or indirectly. Lance guide 112 can be any size required by a particular application, and can preferably include a viewing area 114 for viewing the surface being lanced. Viewing area 114 can be a "window" coupled to the wall of lance guide 112, or as another example, lance guide 112 can be transparent, in whole or in part. Lance guide 112 can, but need not, have a seal 116, such as an annular seal coupled to its bottom end for sealing against a surface being lanced or, as another example, for at least reducing discomfort to a user when system 100 is pressed against an area of the user's body for lancing. Seal 116 can be, for example, a rounded or contoured edge, a soft coating, such as a rubber coating, a pad, a gasket, or another seal, in whole or in part. As another example, in at least one embodiment, which is but one of many, seal 116 can be a suction cup (see, e.g., FIG. 9). Seal 116 can, but need not, be flexible. For example, seal 116 can have an amount of flexibility, so that lance system 100 does not have to be held substantially perpendicular to a lancing surface to assure sealing engagement with the surface. Seal 116 can, but need not, include or be formed from, in whole or in part, a material that has gripping properties, for example, so that if the seal is moved or rotated while in contact with a surface, such as skin, the surface concurrently moves or rotates.

With further reference to FIGS. 1 and 2, system 100 can include a lancing mechanism 118 coupled to lancing end 104, for example, to end cap 108, for supporting a lance 120 (also known as a "lancet"). Lance 120 can include a lance base 120a for supporting a lance needle 120b. Lancing mechanism 118 can include a lancing shaft 122 slideably coupled with end cap 108, such as along central longitudinal axis X, for communicating lance 120 with a surface during lancing. Lancing shaft 122 can include a bottom lance coupling end 124 and a top actuating end 126, and can be any length required by a particular application, as will be further described below. Lancing mechanism 118 can include a lance coupler 128 coupled to lance coupling end 124 for coupling lance 120 to shaft 122, removably or otherwise. For example, lance coupler 128 can be tubular and can form an interference or friction fit with lance base 120a. Lance coupler 128 can, but need not, be adjustable, such as by having a slot or notch at least partially along its length, for example, for coupling to lances of one or more sizes or shapes. As other examples, lance coupler 128 can include threads, screws, notches, or other fasteners for coupling to a lance, as will be understood by one of ordinary skill in the art. Lancing mechanism 118 can include one or more biasing devices, such as a lancing spring 130. Lancing spring 130 can be coupled to lancing shaft 122 for biasing shaft 122 in one or more directions, temporarily, momentarily or otherwise, as will be further described below. Lancing spring 130 can, but need not, comprise a plurality of springs, and can preferably include two springs.

System 100 can include a vacuum mechanism 132 for creating a vacuum and communicating with lancing mechanism 118 or other components of system 100. Vacuum mechanism 132 can include a main shaft 134 having a bottom main actuating end 136, a top main free end 138, and at least one release coupler 140, such as, for example, a notch or indention. Main shaft 134 can be slideably coupled with top end cap 110, for example, so that main actuating end 136 can be disposed inside device body 102 and main free end 138 can be disposed outside device body 102. System 100 can, but need not, include a knob 146, such as a button or cap coupled to main free end 138, for manipulating main shaft 134 or other components. System 100 can include a release mechanism 142, such as a firing device, for communicating with main shaft 134, for example, for releasably coupling with release coupler 140, a series of release couplers, or another portion of main shaft 134. Release mechanism 142 can be any type of releasable coupler, adapted to communicate with main shaft 134, as will be understood by one of ordinary skill in the art. For example, release mechanism 142 can couple with main shaft 134 at one or more positions along its length, such as with release coupler 140, a series thereof or, for example, a notch, groove or outer surface, to releasably hold main shaft 134 in a particular position until, for example, release 144 is actuated, as will be further described below. Vacuum mechanism 132 can include a piston 148 coupled to main shaft 134 for communicating with one or more other components of system 100 to create a vacuum. Piston 148 can be coupled, adjustably, fixedly or otherwise, anywhere on main shaft 134 inside of device body 102, such as, for example, to main actuating end 136. Piston 148 can, but need not, include one or more seals, such as one or more O-rings 150, and can sealingly communicate with interior wall 152 of device body 102, which can, for example, form a vacuum chamber 154 inside device body 102 between piston 148 and a surface to be lanced in communication with seal 116.

System 100 can include one or more openings 156, such as an air passage or orifice, for fluid communication between vacuum chamber 154 and an atmosphere surrounding the vacuum chamber. Opening 156 can be calibrated to allow air to flow into vacuum chamber 154 at a predetermined vacuum dissipation rate, such as, for example, a vacuum dissipation rate less than a predetermined vacuum generation rate in vacuum chamber 154. Opening 156 can be any suitable place for communicating with a vacuum in system 100, such as in device body 102 (see, e.g., FIG. 9), and can preferably, but need not, be in piston 148, separately or in combination. Each opening 156 can, but need not, be adjustable in size, which may include having an adjustable diameter or being interchangeable, separately or in combination. One or more openings 156 can afford any rate of vacuum dissipation required by a particular application, such as a linear rate, non-linear rate, or another rate, in whole or in part, separately or in combination.

Vacuum mechanism 132 can include a biasing device, such as vacuum spring 158, coupled to piston 148 for biasing piston 148 in one or more directions, such as in the upward direction. Vacuum spring 158 can, but need not, include a compression spring disposed between bottom end cap 108 and piston 148 that biases the piston away from bottom end cap 108. Alternatively, or collectively, for example, vacuum spring 158 can include a tension spring that biases piston 148 toward top end cap 110, such as a tension spring disposed between piston 148 and top end cap 110, as will be understood by one of ordinary skill in the art having the benefits of this disclosure. Vacuum spring 158 can, but need not, include a plurality of springs.

System 100 can include a vacuum indicator 133 for indicating whether or to what extent a vacuum exists within vacuum chamber 154. For example, indicator 133 can indicate when a vacuum having at least a predetermined magnitude is present in the system or, as another example, when a vacuum below the predetermined magnitude can be present, including when no vacuum is present. In at least one embodiment, which is but one of many, indicator 133 can be a visual indicator, such as a tab, mark, colored media, notch, or other visible indicator, coupled to main shaft 134, piston 148, or another component, so that indicator 133 can visually indicate, such as by being visible, when no vacuum or a vacuum below a predetermined magnitude is present in the system. Indicator 133 can be visible, for example, through a slot, window, portion of device body 102, or other transparent media, which can be any size or shape. As shown in FIGS. 3A and 3B, for example, indicator 133 may not be visible, such as being inside device body 102, while a vacuum having a predetermined magnitude can be present in the system, and can become visible, such as by passing through a portion of free end 106 and into indicator window 135 when no vacuum or a vacuum below a predetermined magnitude is present in the system. As another example, indicator 133 can be visible through at least a portion of device body 102, through an elongated window disposed longitudinally along device body 102, or through a combination thereof. Alternatively, indicator 133 need not be visible through device body 102 and can be visible only when outside of device body 102, in whole or in part (see, e.g., FIGS. 5A-5E). For example, and without limitation, indicator 133 can be a marking on shaft 134 which only becomes visible outside of device body 102 (e.g., above release mechanism 142) when shaft 134 has sufficiently exited free end 106, so as to indicate that the vacuum has fallen below a predetermined value. In at least one of many alternative embodiments, indicator 133 can be an audible indicator, digital indicator, electrical indicator, electronic indicator or, as other examples, a pressure sensitive indicator or mechanical indicator, separately or in combination. Indicator 133 can, but need not, indicate to a user when a vacuum in system 100 during lancing is sufficiently dissipated (i.e., is of sufficiently low magnitude) that system 100 can be removed from a surface being lanced. For example, in an application where skin is being lanced for purposes of drawing blood, indicator 133 can indicate when system 100 can be removed from the skin so that the drawn blood does not splatter, such as could happen due to an inrush of atmospheric air, e.g., if seal 116 were to be lifted off the skin with a relatively high vacuum in vacuum chamber 154.

System 100 can include a shaft coupler 160 for releasably coupling one or more components of system 100, such as lancing shaft 122 and main shaft 134. Shaft coupler 160 can include two or more portions that optionally communicate with one another. For example, shaft coupler 160 can include a first portion 160a coupled to lancing shaft 122, such as to actuating end 126, and a second portion 160b coupled to main shaft 134, such as to main actuating end 136. First portion 160a and second portion 160b can be adapted to releasably couple to one another when brought at least proximate to one another and to uncouple upon a predetermined event, for example, when a sufficient force applied to shaft coupler 160. In at least one embodiment, which is but one of many, one of portions 160*a*, 160*b* can be a magnet and the other portion can be magnetic material, which can allow, for example, lancing shaft 122 and main shaft 134 to remain coupled until a separation force, such as a tensile force, is applied sufficient to overcome the coupling force between first portion 160*a* and second portion 160*b*. Alternatively, or collectively, either portion 160*a*, 160*b* can be a portion of one of the shafts 122, 134, such as one of the actuating ends 126, 136, or, as another example, second portion 160*b* can be coupled to, including formed integrally with, piston 148. In at least one other embodiment, which is but one of many, first and second portions of shaft coupler 160 can include hook and loop material, mechanical fasteners, ball and joint unions, sticky material, or other couplers, as required by a particular application. In at least one embodiment, which is but one of many, a sufficient separation force can be any force less than a force generated by the vacuum spring 158 (see, e.g., FIG. 2).

With reference to FIG. 4, lancing mechanism 118 can, but need not, include bottom end cap 108. Alternatively, lancing mechanism 118 can be separately coupled to bottom end cap 108 or another portion of lancing end 104 of device body 102. Lancing spring 130 can include a plurality of springs, such as upper spring 130*a* and lower spring 130*b* (collectively referred to herein as lancing spring 130). Lancing mechanism 118 can include a stop 129, such as a tab or block, for supporting lancing spring 130 or defining the stroke of lancing shaft 122, in whole or in part. In at least one embodiment, such as the embodiment shown in FIG. 4, which is but one of many, stop 129 can be disposed between lance coupling end 124 and actuating end 126 of lancing shaft 122. Upper spring 130*a* can be coupled between stop 129 and actuating end 126, and lower spring 130*b* can be coupled between stop 129 and lance coupling end 124. Each lancing spring 130*a*, 130*b* can be loosely disposed about shaft 122 or can have one or more ends fixedly coupled to shaft 122 or stop 129, separately or in combination. Each lancing spring 130*a*, 130*b* can be any type of spring, or other biasing device, and can have any K value or length required by a particular application. Lancing shaft 122 can have a resting state, which can be at least partially defined by communication between springs 130*a*, 130*b* and stop 129, separately or in combination with one or more other components of system 100. For example, when shaft 122 is at rest, one or more of springs 130*a*, 130*b* can, but need not, be in their natural state (i.e., neither compressed nor extended). Alternatively, one or more springs can be under tension or compression when lancing shaft 122 is at rest or, as another example, while lancing shaft 122 is in motion, such as during lancing, as required by a particular application and as will be understood by one of ordinary skill. When lancing shaft 122 is in a rest position, lance needle 120*b* can, but need not, be distal from a surface 168 being lanced, such as skin (see, e.g., FIG. 5F). Lancing shaft 122 can be any length required by a particular application and can be slideably coupled with stop 129 so that lancing spring 130 can bias shaft 122, such as in the upward or downward direction, as will be further described below.

Figure 5H:
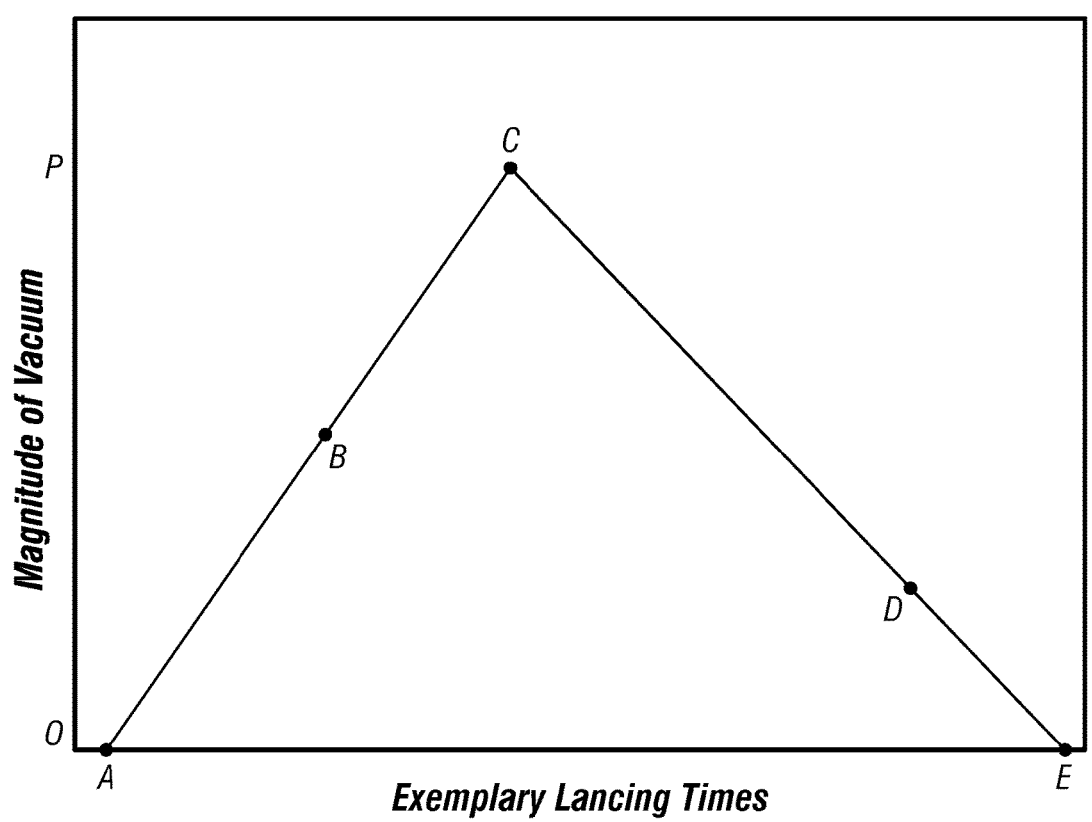
FIG. 5H is a graph illustrating the vacuum magnitude versus the time over which lancing can occur during a vacuum cycle.

FIG. 5A is an illustration of one of many embodiments of a vacuum lance system 100 in a cocked position according to the disclosure. FIGS. 5B, 5C and 5D are illustrations of the system 100 of FIG. 5A in three respective positions during lancing. FIG. 5E is an illustration of the system 100 of FIG. 5A in an uncocked position. FIG. 5F is an illustration of the system 100 of FIG. 5A manipulating a surface during lancing. FIG. 5G is an illustration of the system 100 of FIG. 5A vibrating a surface during lancing. At least one of many methods of using the embodiment of system 100 shown in FIGS. 5A-5G can be described. FIG. 5H is a graph illustrating the vacuum magnitude versus the time over which lancing can occur during a vacuum cycle. FIGS. 5A-5H will be described in conjunction with one another.

A lance 120 can be coupled to lancing mechanism 118, such as by using one of the methods described herein, for example, before or after system 100 is in a "cocked" position (see, e.g., FIG. 5A). System 100 can be cocked, for example, by pressing knob 146 downward until at least a portion of main shaft 134, such as release coupler 140, couples with release mechanism 142, which can releasably hold main shaft 134 and piston 148 downwardly toward lancing end 104, such as against the force of vacuum spring 158. Shaft coupler second portion 160*b* on main actuating end 136 can couple to first portion 160*a* of shaft coupler 160 on actuating end 126 of lancing shaft 122. Actuating end 126 can, but need not, move downwardly during cocking, temporarily or otherwise. Upper spring 130*a* and lower spring 130*b* can, but need not, be in their natural states. System 100 can engage a surface to be lanced (not shown), such as to an area of skin on a person's body, which can be any area. For example, seal 116 on lance guide 112 can engage the surface so that at least a partially airtight seal is formed between seal 116 and the surface.

System 100 can be activated, or fired, for example, by actuating release 144, which can at least partially uncouple main shaft 134 and, for example, release coupler 140, from release mechanism 142, which can allow main shaft 134 to slideably communicate with top end cap 110. Release 144 can be pressed directly, such as with a user's finger, or indirectly actuated, for example, using a magnet, electrical or mechanical actuator, or another method, as required by a particular application. Vacuum spring 158 can at least partially decompress (or lose tension if a tension spring, as described above) and piston 148, main shaft 134 and shaft coupler 160 can move in the upward direction away from the surface being lanced. Piston 148, which can, but need not, include one or more seals, such as O-rings 150, can be in sliding sealing engagement with interior wall 152 of device body 102, thereby at least partially forming a vacuum in vacuum chamber 154 as piston 148 moves away from the surface being lanced. One or more components of lancing mechanism 118, such as actuating end 126 and lancing shaft 122 can move upward with main shaft 134, for example, due to the coupling force of shaft coupler 160 and the force of expanding vacuum spring 158. Upper spring 130*a* can expand and lower spring 130*b* can contract, which can, for example, singularly or in combination, exert an increasing force on first portion 160*a* of shaft coupler 160 in the opposite direction (e.g., downward) of the force exerted on second portion 160*b* by vacuum spring 158 (e.g., upward) as vacuum spring 158 expands (FIG. 5B). Lancing shaft 122 can have a shorter stroke than main shaft 134. For example, stop 129 can limit the stroke of lancing shaft 122, for example, by preventing at least a portion of shaft 122 from traveling upward past the stop or, as another example, lancing spring 130 (referring collectively to springs 130*a* and 130*b*) can be arranged to limit the stroke of lancing shaft 122, separately or in combination with stop 129. In at least one embodiment, which is but one of many, lancing spring 130 can have, for example, a length or K-value that can result in a lancing spring force greater than the coupler force of shaft coupler 160 when lancing shaft 122 is in a particular position, which can be any position required by a particular application.

Shaft coupler 160 can uncouple and second portion 160*b* can continue moving in the upward direction (FIG. 5C). Piston 148 can continue moving upward during and after penetration of the surface, continuously or in segments, such as by using two or more release couplers 140 that successively couple to release mechanism 142, which can increase the vacuum to which the surface can be exposed. Upper spring 130*a* can contract and lower spring 130*b* can expand, singularly or in combination, which can, for example, cause first portion 160*a* to move in the opposite (i.e., downward) direction from second portion 160*b* of shaft coupler 160. Lancing shaft 122 may be drawn back away from the surface and the coupling force between portions 160*a* and 160*b* may be overcome. Lancing mechanism 118 can move toward a rest position, such as due to the force of one or more springs 130. Lancing shaft 122 can move downwardly, such as until at least a portion of lance 120 contacts the surface (FIG. 5D). In at least one embodiment, which is but one of many, lancing shaft 122 can, but need not, move downwardly far enough that upper spring 130 at least partially compresses and lower spring 130*b* at least partially expands as lance 120 lances the surface. As will be understood by one of ordinary skill, inertia may cause lancing shaft 122 to move past its rest position (e.g., downward), for example, so that lance needle 120*b* may pierce the surface, before returning to its rest position. After at least partially penetrating the surface, each of springs 130*a*, 130*b* and lancing shaft 122 can return to a state of rest (FIG. 5E), and lance 120 can be disposed upwardly and distally from the surface.

The surface can be subjected to a vacuum before, during, or after lancing, separately or in combination. Air can enter vacuum chamber 154, such as through opening 156, which can dissipate the vacuum at any rate required by a particular application. Indicator 133, such as a tab, groove, or mark, can become visible, such as by passing outside of device body 102, which can indicate dissipation of the vacuum, in whole or in part. System 100 can be disengaged from the surface, which can leave a quantity of blood on the surface for collection.

A surface 168 being lanced can, but need not, be manipulated during lancing, which can include twisting, pumping, pressing up and down, or any movement, separately or in combination (see, e.g., FIG. 5F). For example, where surface 168 is skin, one or more components on lancing end 104 of device body 102, such as lance guide 112 or seal 116, can be used to knead, massage or otherwise manipulate the skin at any time during the lancing process, for example, before, during or after the skin is lanced, which can result in a greater volume of blood 176 being extracted and/or more rapid blood extraction. As an example of this manipulation, seal 116 can be placed against the skin and twisted in one or more directions, such as back and forth, clockwise, then counterclockwise (or vice versa), for example, so that the skin twists, such as due to friction between the skin and seal 116, which can increase blood flow to the area being lanced or out of an opening in the skin made by lance 120. The surface of seal 116 can be made of or coated with a gripping type substance, such as to aid in twisting the surface when seal 116 is being twisted. Another example of this manipulation, which can speed up blood drawing, can include increasing and decreasing inward pressure of seal 116 on the surface in a pulse-like action. Each of these classes of manipulation, just as with squeezing a finger if it is pricked, can speed up blood flowing through a lance-generated hole. This can be especially true in the presence of a vacuum on the surface as described in the present disclosure. The degree of manipulation, if any, of the skin can vary from surface to surface on areas of the user, and from user to user, as will be understood by one of ordinary skill having the benefits of this disclosure.

With continuing reference to FIGS. 5A-5G, and further reference to FIG. 5H, the timing and magnitude of vacuum creation and lancing can include one or more variables, as will be understood by one of ordinary skill, each of which can have any value required by a particular application. The magnitude of the vacuum and the rate at which the vacuum can be created, the timing of lancing, such as when shaft coupler 160 uncouples, the rate at which lance 120 can travel, and the force with which lance 120 strikes a surface, or other factors can, but need not, be optimized for a particular application. Further, the vacuum creation can occur in a single stage, or in multiple stages. For example, one or more of these factors can be correlated with travel and timing of the piston 148 along a length of device body 102. As will be understood by one of ordinary skill in the art, the further piston 148 travels within device body 102 (e.g., away from a surface being lanced), the higher a vacuum in vacuum chamber 154 may be. Further, the force with which lance 120 contacts a surface, such as skin, can be at least enough to puncture or penetrate the surface, and can advantageously drive at least a portion of needle 120*b* through the surface and into subcutaneous tissue beneath the surface from which blood may be taken. One or more variables can be defined by the length and/or K value of a spring, such as of lancing spring 130 or vacuum spring 158, the volume of vacuum chamber 154 or, as another example, by the weight, stroke or length of a shaft, such as lancing shaft 122 or main shaft 134.

In at least one embodiment, such as the embodiment shown in FIGS. 5A-5G, which is but one of many, the stroke of lancing shaft 122 can determine when shaft coupler 160 can uncouple during lancing and when lance 120 can contact or penetrate the surface being lanced, such as during a period of time in which a vacuum can be applied to the surface. For example, upon release from a cocked position, piston 148 can travel upward from a lowermost position (see, e.g., FIG. 5A) where no vacuum exists within vacuum chamber 154 to an uppermost position (see, e.g. FIG. 5E), thereby creating a maximum vacuum within vacuum chamber 154, which can be any magnitude of vacuum, such as up to 30 inches of mercury, required by a particular application.

As shown for illustrative purposes in FIG. 5H, lancing of a surface can occur at any time before, during, or after a vacuum cycle, as may be suitable for a particular application. For example, the lancing of the surface can occur before a vacuum is created, as indicated by reference A. Alternatively, the lancing of the surface can occur while the vacuum is increasing in the device body, as indicated by reference B, such as at ½ of peak vacuum P. As will be understood by one of ordinary skill having the benefits of this disclosure, reference B illustrates one of many lancing times during vacuum creation, and lancing can alternatively occur at any point along a line between references A and C. The lancing can also occur when the vacuum is at peak vacuum P, illustrated by reference C. In one or more other embodiments, lancing may occur after peak vacuum and before the vacuum has been entirely dissipated, such as at a point in time illustrated by reference D, which may be, for example, ⅓ P, or any point in time along a line between references C and E. As another example, lancing may occur after a vacuum has dissipated, such as at the point in time illustrated by reference E.

As described above, lancing can occur at any time during a vacuum cycle, including before, during, or after a vacuum is created, and can advantageously occur when at least a partial vacuum is created, such as between 30% and 70%, or any increment there between, of the maximum vacuum for a particular application. In at least one embodiment, which is but one of many, lancing can preferably occur at between 40% and 60% of vacuum creation, or any increment there between, such as at 50% vacuum creation. For example, the maximum vacuum can be −20 inHg, and the surface can be lanced when the vacuum in vacuum chamber 154 is, for example, −10 inHg. However, this need not be the case, and the examples described herein are for illustrative purposes. The timing of lancing can, but need not, be adjustable. For example, in at least one embodiment, such as a commercial embodiment, which is but one of many, system 100 can include a plurality of interchangeable lancing shafts, each of which can have a different length, which can determine when lancing occurs during a vacuum cycle, as described above.

The rate at which the vacuum is created, which can be determined by the rate at which piston 148 travels upward, can, but need not, be adjustable. For example, in at least one embodiment, system 100 can include a shock absorber, piston or other device (not shown), for controlling the rate at which piston 148 ascends during lancing. The vacuum can be dissipated, or released, such as through opening 156, or movement of piston 148, separately or in combination, at any rate required by a particular application. For example, where the surface being lanced is skin, the vacuum can advantageously be released at a rate that may allow an adequate amount of blood for collecting to be drawn from the surface or, as another example, at a rate that can at least partially minimize blood splatter when the system is removed from the skin.

With continuing reference to FIGS. 5A-5G, system 100 can, but need not, be adapted to vibrate during lancing. The term "vibrate" and conjugations thereof are used broadly herein and specifically include, without limitation, any shake, quiver, pulsation, or other movement applied by lance system 100 to a surface being lanced. One or more vibrations can be timed to occur in proximity (e.g., in time and space) to lance penetration of a surface, which can mask the sensation of penetration from the user. Vibration in system 100 can at least partially mask pain associated with lancing, if any, such as where the surface being lanced is skin. The vibration can be controlled by adjusting properties of one or more of the components, such as the dynamic components, of a particular embodiment of system 100, and can have any magnitude or duration required by a particular application. The magnitude of a vibration can depend on, or be predetermined by, for example, the mass of one or more components in the system, the K value of one or more springs, the stroke of one or more shafts, the momentum of one or more components, or other factors, as will be understood by one of ordinary skill having the benefits of this disclosure. One or more vibrations can occur singularly, consecutively, concurrently, supplementary or otherwise, and can occur in, or transfer to, one or more components of system 100. Advantageously, one or more vibrations may be present at lancing end 104, for example, so that the vibrations can at least partially transfer to surface 168 during lancing (see, e.g. FIG. 5G), which can thereby aid in masking the pain of lancing. The vibration can be caused by any of the components, such as the dynamic components, of a particular embodiment of system 100, and can have any magnitude or duration required by a particular application. The magnitude of a vibration can depend on, or be predetermined by, for example, the mass of one or more components in the system, the K value of one or more springs, the stroke of one or more shafts, the momentum of one or more components, or other factors, as will be understood by one of ordinary skill having the benefits of this disclosure. In at least one embodiment, which is but one of many, a vibration can begin before penetration of a surface, and can, at least partially, continue during penetration of the surface. The vibration can advantageously, but need not, continue after the surface has been lanced. As other examples, one or more components of lancing mechanism 118, such as lancing spring 130 or lancing shaft 122, can cause vibration in system 100, separately or in combination with other components in the system.

In at least one embodiment, which is but one of many, one or more portions of the lancing assembly, such as lancing shaft 122, lance coupler 128, or main shaft 134, can move in a first direction, such as toward free end 106 of device body 102, for example, over a first distance. One or more of the portions, such as first portion 160a of shaft coupler 160, can be stopped from moving further in the first direction, such as further than the first distance, for example, by stop 129, which can cause a vibration in one or more parts of system 100. Advantageously, the vibration continues to occur for an amount of time at least long enough for the surface to be penetrated. One or more components can move in a second direction, such as in a direction opposite the first direction, for example, toward the lancing end 104 of device body 102. The one or more components, such as lancing shaft 122 or first portion 160a of shaft coupler 160, can be stopped from further moving in the second direction, for example, past a second distance, which can cause one or more vibrations in system 100.

Figure 6:
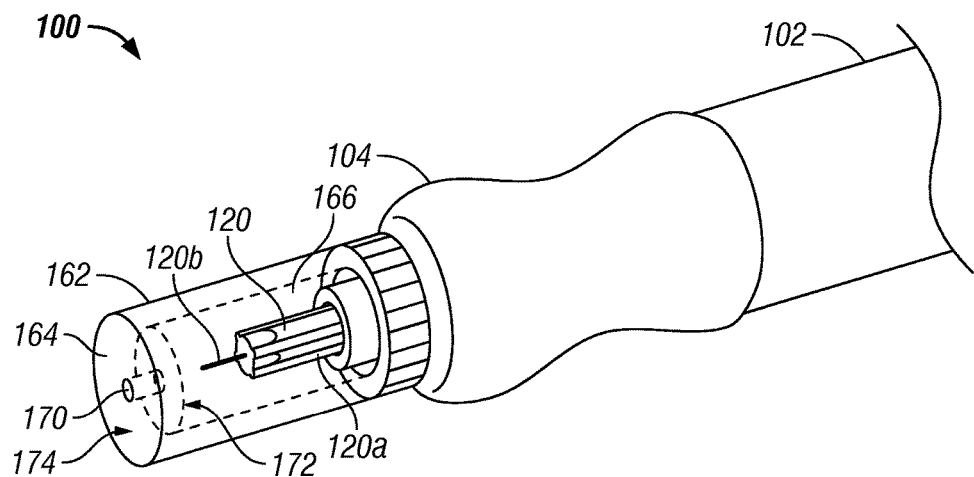
FIG. 6 is a front isometric schematic view of one of many embodiments of a vacuum lance system having a depth controller according to the disclosure.
Figure 7A:
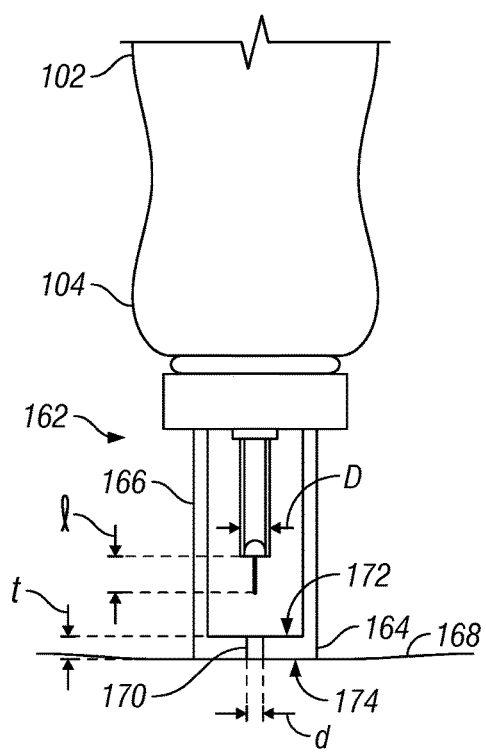
FIG. 7A is a cross-sectional schematic view of the system of FIG. 6.
Figure 7B:
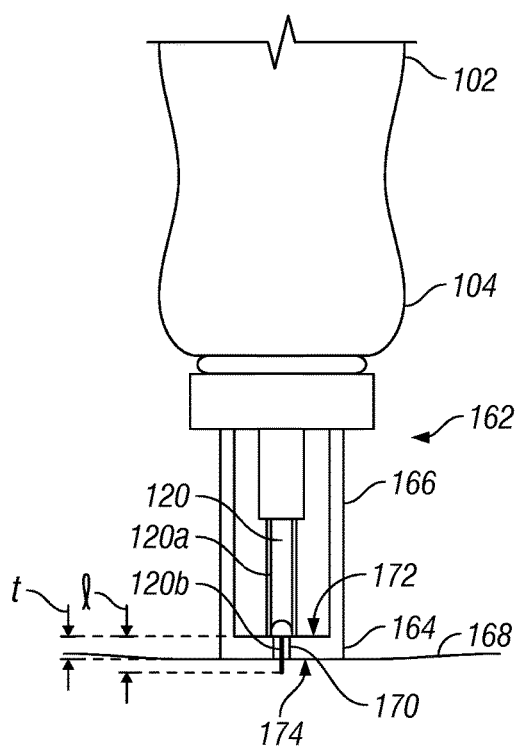
FIG. 7B is a cross-sectional schematic view of the system of FIG. 6 with a base contacting a spacer.
Figure 7C:
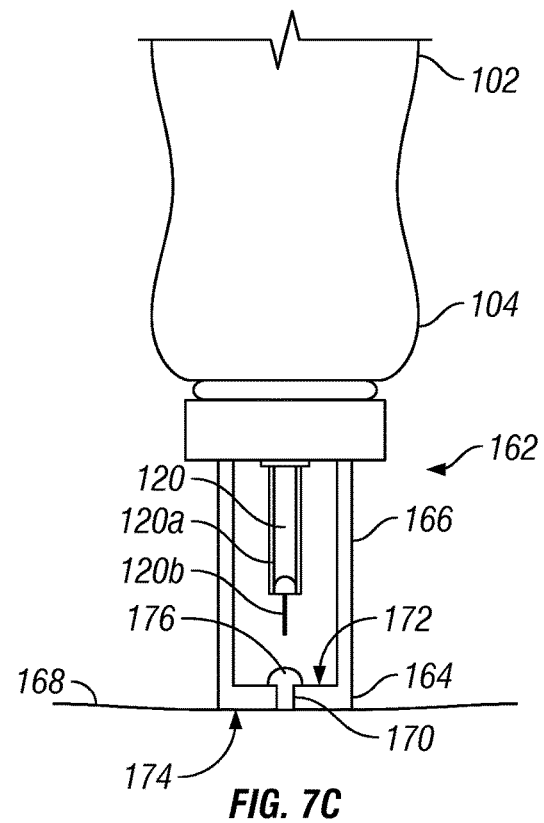
FIG. 7C is a cross-sectional schematic view of the system of FIG. 6 during blood extraction.

FIG. 6 is a front isometric schematic view of one of many embodiments of vacuum lance system 100 having a depth controller 162 according to the disclosure. FIG. 7A is a cross-sectional schematic view of the system 100 of FIG. 6. FIG. 7B is a cross-sectional schematic view of the system 100 of FIG. 6 with a base contacting a spacer. FIG. 7C is a cross-sectional schematic view of the system 100 of FIG. 6 during blood extraction. FIGS. 6-7C will be described in conjunction with one another. Vacuum lance system 100 can include a depth controller 162 for controlling the depth to which a surface is lanced during lancing. Depth controller 162 can include a calibrated spacer 164 and a spacer coupler 166 for coupling spacer 164 to lancing end 104 of device body 102. Depth controller 162 can be formed from any material, such as plastic or metal, and can be replaceably and interchangeably coupled to device body 102 in any manner, such as being threaded thereon, forming an interference or friction fit with one or more other components of system 100, or fastened with fasteners, such as screws, brackets, adhesive, or other fasteners, removably, permanently or otherwise, and other method of attachment. Alternatively, depth controller 162 can be fixedly coupled to device body 102, integrally or otherwise, or any portion thereof. Depth controller 162 can, but need not, be transparent, in whole or in part. Spacer coupler 166 can be tubular and can be coupled, for example, to lance guide 112 (see, e.g., FIG. 1) or, as another example, in place of lance guide 112, as required by a particular application. Spacer 164 can be coupled to spacer coupler 166, including being formed integrally therewith, between lance 120 and a surface 168 being lanced.

Spacer 164 can include a central opening, such as hole 170, for allowing at least a portion of lance 120 to pass there through, and can have a calibrated thickness "t", which can be any thickness required by a particular application, and which can be the same or different from the thickness of one or more portions of spacer coupler 166. Spacer 164 can, but need not, be adjustable, which can include being interchangeable, individually or simultaneously with spacer coupler 166, for example, to allow for spacers of different thicknesses. Hole 170 (having dimension "d" in FIG. 7A) can have any shape or cross-sectional area required by a particular application, and can advantageously have a cross-sectional area larger than that of needle 120b and smaller than that of base 120a (having dimension "D" in FIG. 7A) so that needle 120b can pass through hole 170 and base 120a can not, i.e., D>d (see, e.g., FIG. 7B). Base 120a can contact the upper surface 172 of spacer 164 during lancing, which can limit the depth to which needle 120b can penetrate surface 168, such as to the difference between length "l" of needle 120b and the thickness "t" of spacer 164. This can be advantageous, for example, because the depth of penetration of needle 120b into surface 168 can be controlled regardless of the force with which lance 120 travels in the downward direction during lancing, which can be any force. For example, where the surface 168 is skin, the force required to thrust lance 120 into the skin can vary from application to application and user to user, such as between relatively soft or thin skin and relatively tough or thick skin, such as, for example, calloused skin.

Depth controller 162 can allow, for example, a relatively large force, such as a force large enough to lance calloused skin, to also be used on softer areas of skin, for example, by stopping the travel distance of needle 120b, so that regardless of its toughness, skin can be lanced to a depth of "l" minus "t" when the bottom surface 174 of the spacer 164 is adjacent the skin, i.e., a depth equal to the difference between the length "l" of lance needle 120b and the thickness "t" of spacer 164. As another advantageous example, where the surface 168 being lanced is skin, a blunt force or vibration can result, such as from an impact between upper surface 172 and base 120a, which can, but need not, mask pain that can result from lancing. In at least one embodiment, which is but one of many, and is described herein only for illustrative purposes, lance 120, which can, but need not, be an off-the-shelf commercially available lance, can have a base 120a having a dimension "D" (which can, but need not, be a diameter) of 0.250" and a lance needle 120b having a length "l" of 0.125". Spacer 164 can have a thickness "t" of 0.035" and a hole 170 having a dimension "d" of 0.200". As will be understood by one of ordinary skill having the benefits of this disclosure, this illustrative embodiment, for example, can penetrate the surface 168 being lanced up to 0.090" which is the difference between the exemplary length "l" of needle 120a and the exemplary thickness "t" of spacer 164.

The thickness "t" of spacer 164 can be any thickness required by a particular application, wherein the greater the thickness "t", the lesser the lance penetration depth, and vice versa, for a particular length "l" of a needle 120a required by a particular application. The thickness "t" of a particular spacer 164 can preferably allow at least a portion of needle 120b to penetrate surface 168, such as skin or another lancing surface, so that blood 176 may leave surface 168. Spacer 164 can be calibrated for any surface, such as for one or more areas of a user's skin. For example, spacer 164 can be relatively thin for some surfaces, such as where blood vessels are scarce or more distant from the surface of the skin, or spacer 164 can be relatively thick for other surfaces, for example, where blood may be closer to the skin, which can vary from application to application, or from user to user. Bottom surface 174 of spacer 164 can, but need not, be in direct contact with a lancing surface, for example, for allowing hole 170 to sealingly engage the surface. In at least one embodiment, for example, depth controller 162 can include an annular rim (not shown), which may comprise a seal, coupled to bottom surface 174 and extending downwardly to engage a lancing surface, singularly or in combination with bottom surface 174.

Depth controller 162 can include interchangeable or modular units, which can include interchangeable spacers 164 for a particular depth controller 162 or, as another example, interchangeable depth controllers 162 for a particular system 100, wherein one or more depth controllers 162 can, but need not, have spacers 164 of different calibrated thicknesses. Each interchangeable unit can be graduated and can, for example, vary incrementally from unit to unit. In at least one embodiment, which is but one of many, system 100 can include a plurality of depth controllers 162, such as a set or kit, which can include a plurality of different depth controllers or spacers that can be selectively changed or switched by a user as required by a particular application. In at least one embodiment, which is but one of many, a set of depth controllers 162 may be stored, or storable, in a container, such as a bag or case, such as when not in use. A user can choose to use any of one or more depth controllers 162 required by a particular application, which can include choosing to use a depth controller already coupled to device body 102 or, as another example, can include choosing a depth controller separate from device body 102 and coupling the chosen depth controller to device body 102.

Figure 8A:
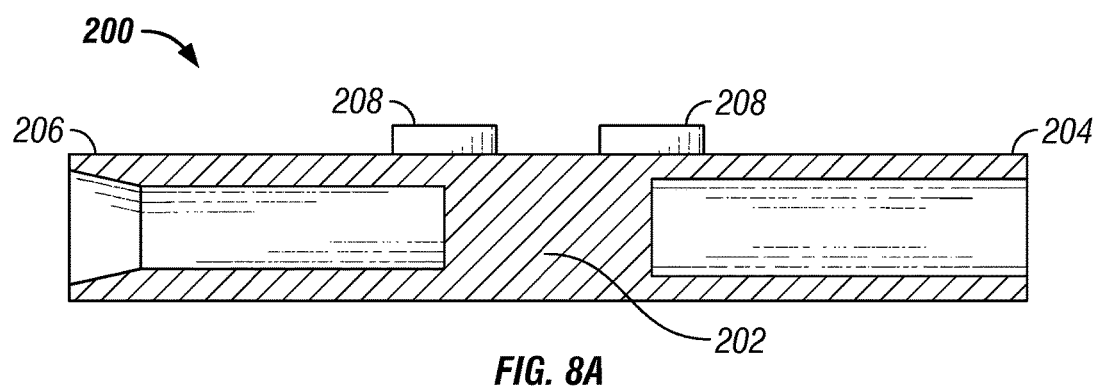
FIG. 8A is an illustration of one of many embodiments of a vacuum lance system having a lance tool according to the disclosure.
Figure 8B:
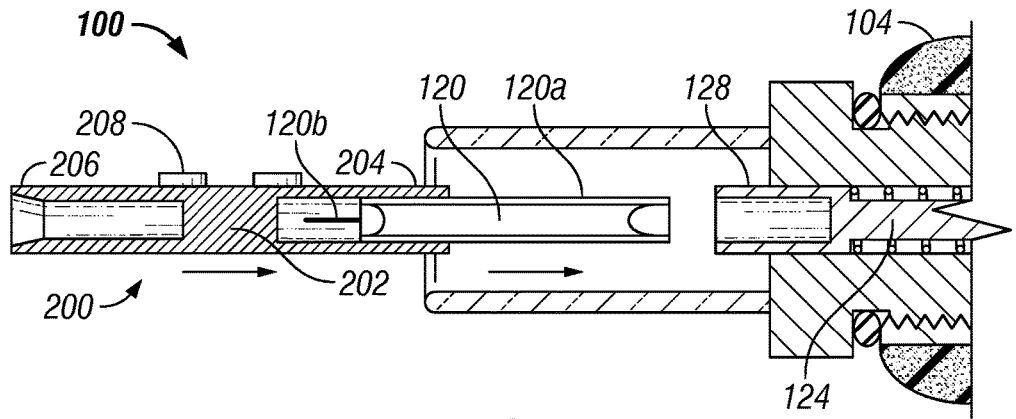
FIG. 8B is an illustration of a lance being inserted into a lance coupler with the lance tool of FIG. 8A.
Figure 8C:
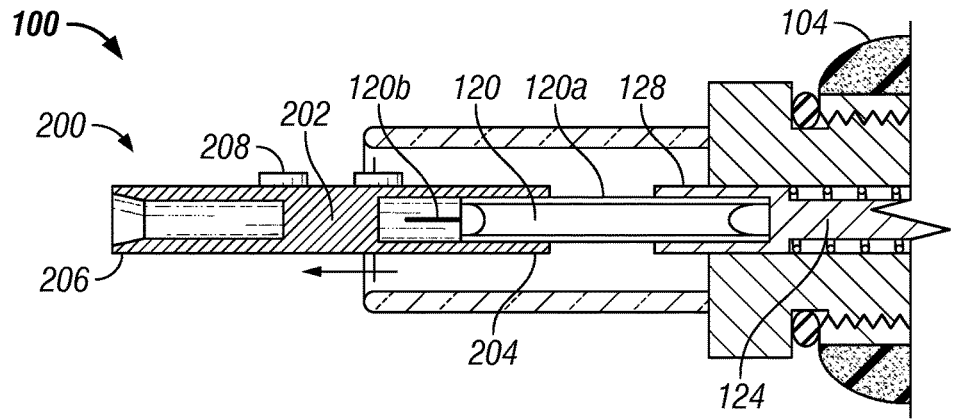
FIG. 8C is an illustration of a lance being coupled to the lance coupler with the lance tool of FIG. 8A.
Figure 8D:
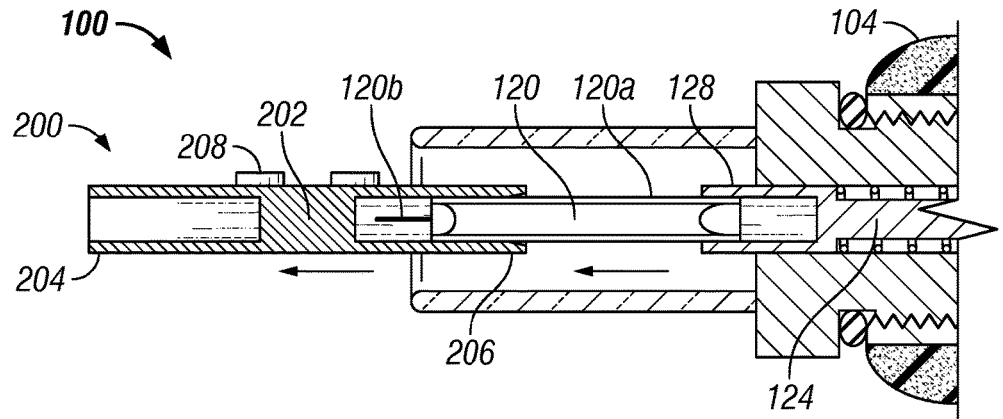
FIG. 8D is an illustration of a lance being removed from the lance coupler with the lance tool of FIG. 8A.

FIG. 8A is an illustration of one of many embodiments of a vacuum lance system having a lance tool 200 according to the disclosure. FIG. 8B is an illustration of a lance 120 being inserted into lance coupler 128 with lance tool 200. FIG. 8C is an illustration of a lance 120 being coupled to lance coupler 128 with lance tool 200. FIG. 8D is an illustration of a lance 120 being removed from lance coupler 128 with lance tool 200. FIGS. 8A-8D will be described in conjunction with one another. Vacuum lance system 100 can include a lance tool 200 for coupling and uncoupling a lance 120 with lance coupling end 124 of lancing shaft 122, such as to lance coupler 128, safely and conveniently. Lance tool 200 can include a lance tool body 202 and one or more couplers, such as, for example, lance insertion coupler 204 and lance removal coupler 206, which can, but need not, be tubular. For example, insertion coupler 204 and removal coupler 206 can, but need not, have annular cross-sections and/or one or more longitudinal slots to allow lance 120 to be inserted therein, as will be understood by one of ordinary skill.

To install lance 120 into system 100, for example, lance 120 can be inserted into insertion coupler 204 "needle end first" so that the needle 120b of lance 120 is inside insertion coupler 204 and so that base 120a of lance 120 couples with insertion coupler 204 and at least a portion of base 120a protrudes from insertion coupler 204 (see, e.g., FIG. 8B). In at least one embodiment, which is but one of many, base 120a and insertion coupler 204 can form a clearance fit or, as another example, an interference fit less than an interference fit between lance coupler 128 and base 120a. Insertion coupler 204 and lance 120 can be moved toward lancing end 104, as indicated by the arrows in FIG. 8B, and disposed so that the portion of base 120a protruding from insertion coupler 204 couples with lance coupling end 124 of lancing shaft 122, such as to lance coupler 128 (see, e.g., FIG. 8C). For example, as mentioned above, lance base 120a can form an interference fit with lance coupler 128 so that lance 120 uncouples from insertion coupler 204 and remains seated in lance coupler 128 for lancing when lance tool 200 is removed from lance guide 112, as indicated by the arrow in FIG. 8C.

To remove lance 120 from lance coupler 128, for example, lance removal coupler 206 can be inserted into lance guide 112 until removal coupler 206 passes over needle 120b and couples to base 120a of lance 120. For example, removal coupler 206 and base 120a can form an interference fit, such as an interference fit having a greater interference (i.e., a tighter fit) than the interference fit formed between base 120a and lance coupler 128. Lance tool 200 and lance 120 can be moved away from lance coupler 128, as indicated by the arrows in FIG. 8D, and lance 120 can uncouple from lance coupler 128 and remain coupled to removal coupler 206, which can remove lance 120 from lance coupling end 124. Although lance insertion coupler 204 and lance removal coupler 206 of the lance tool 200 have been described herein to communicate with lance 120 using one or more "fits," such as an interference or clearance fit, this need not be the case, and, alternatively, each coupler 204, 206 can communicate with lance 120 in any manner required by a particular application, as will be understood by one of ordinary skill in the art. As one example, which is but one of many, lance 120 can threadably couple to lance coupler 128, and one or more of couplers 204, 206 of the lance tool 200 can include a notch, groove, or other structure for communicating with lance 120, such as in a complementary fashion, separately or in combination with a particular fit, for example, for screwing lance 120 into or unscrewing lance 120 from lance coupler 128.

In at least one embodiment of lance system 100, which is but one of many, lance tool 200 can be coupled to lance device body 102, such as to the exterior along its length, when not in use. For example, lance device body 102 or lance tool 200 can, but need not, have at least one holder 208, such as complementary couplers, mounted thereon, such as, for example, magnets, hook and loop material, snaps or other fasteners. As other examples, device body 102 can have a hook, brace, grip or other holder coupled thereto and adapted to hold lance tool 200, such as by tool body 202, or device body 102 can have a stud or bracket adapted to couple to insertion coupler 204 or removal coupler 206. Lance tool 200 can be formed from any material required by a particular application, such as plastic, metal or another material, and can be any shape or size, as will be understood by one of ordinary skill in the art having the benefits of this disclosure.

FIG. 9 is a cross-sectional schematic view of one of many embodiments of a vacuum lance system 300 having an external vacuum indicator 302 according to the disclosure. For purposes of clarity, the same reference numerals as those used previously herein will be used in some instances, while new reference numerals will be used to reference components that may not have been described above. It should be understood that although the same reference numeral may be used to reference a component in two or more Figures, the component can, but need not, be exactly the same in practice, as required by a particular embodiment or application.

Lance system 300 can generally function similarly to one or more of the other embodiments described herein, and can include an external vacuum indicator 302 coupled to device body 102 for indicating whether a vacuum is present in the system. Indicator 302 can include an indicator body 304 coupled in fluid communication with vacuum chamber 154, such as with indicator air tube 306, which may be any type of conduit. Indicator 302 can include a marker 310 sealingly coupled inside indicator body 304 and an indicator spring 308 coupled between marker 310 and vacuum chamber 154. Indicator 302 can include a viewing window 312 for viewing marker 310, such as, for example, when no vacuum exists in the system. Window 312 can be coupled anywhere to indicator body 304, for example, to the top or side, and can be any size. For example, window 312 can, but need not, be at least a portion of indicator body 304 and can be at least partially transparent, such as a thin transparent strip along the length of indicator body 304. Alternatively, for example, indicator body 304 can be wholly transparent.

Indicator 302 can be coupled to device body 102 in any location between a surface being lanced and piston 148. Indicator 302 can be an "L-type" indicator (as shown in FIG. 9), for example, so that indicator body 304 is parallel to device body 102, a "T-type" indicator, for example, so that indicator body 304 is perpendicular to device body 102 or, as another example, indicator 302 can be disposed at another angle, which can be any angle, relative to central longitudinal axis X of the system.

As a vacuum is created in system 300 during lancing, marker 310, such as a disk or other indicator, can travel toward tube 306, and, for example, spring 308 can be compressed. Marker 310 can, but need not, become invisible. As the vacuum is released during lancing, marker 310 can move along tube 306 and spring 308 can expand, which can move at least a portion of marker 310 into view, such as being visible through window 312. While indicator spring 308 can be shown to be a compression spring in FIG. 9 for illustrative purposes, it need not be, and can alternatively be a tension spring, or both, separately or in combination, as will be understood by one of ordinary skill.

With further reference to FIG. 9, system 300 can include at least one opening between vacuum chamber 154 and an atmosphere surrounding the vacuum chamber, as described above (see, e.g., FIG. 5A). For example, and without limitation, the embodiment of FIG. 9, which is but one of many, can include three openings 156A, 156B and 156C (collectively "opening 156"), but this need not be the case and, alternatively, system 300 may include any number of openings 156, such as one, two, or more, or none, as required by a particular application. Each opening 156, such as one or more of openings 156A-C, can be in piston 148, device body 102, or another portion of system 300, separately or in combination. Like the embodiment of FIG. 9, any embodiment of the present invention, such as one or more of the other embodiments shown or described herein, may include any number of openings 156 disposed in any location required by a particular application, separately or in combination, as will be understood by one of ordinary skill having the benefits of the present disclosure. While one or more openings 156 in a particular embodiment can afford a linear vacuum dissipation rate (see, e.g., FIG. 5H), this need not be the case and, alternatively, a rate of vacuum dissipation can be non-linear, as required by a particular application.

FIG. 10 is a cross-sectional schematic view of one of many embodiments of a vacuum lance system 400 having an external vacuum assembly 402 according to the disclosure. System 400 can include a lancing assembly 404 for lancing a surface, which can be any lancing assembly required by a particular application. Lancing assembly 404 can, but need not, include a vacuum mechanism coupled with main device body 408, such as, for example, one or more of the embodiments described herein, partially, separately or in combination. System 400 can include a lance 120, such as a commercially available lance, and a vacuum chamber 406, which can, but need not, extend at least partially inside main device body 408. System 400 can include an external vacuum assembly 402 for at least partially creating a vacuum in vacuum chamber 406. Vacuum assembly 402 can, but need not, be a second, additional or supplementary source of vacuum in system 400, and can operate separately or in combination with one or more other components, such as vacuum components, lancing components, or other components of system 400.

Vacuum assembly 402 can include a vacuum body 410 for supporting one or more components of the system. Vacuum body 410 can be tubular and can have a vacuum end 412 and a longitudinally opposite end 414. Vacuum body 410 can, but need not, be coupled to main device body 408, rigidly, removably, or otherwise. Vacuum assembly 402 can include a shaft 416, which can be slideably coupled to end 414. Vacuum assembly 402 can include a release mechanism 418 coupled, for example, to end 414 of vacuum body 410, which can communicate with shaft 416 to removably hold shaft 416 or one or more other components in one or more positions. Vacuum assembly 402 can include a piston 420, which can be in sealing engagement with vacuum body 410, such as with an inner surface 422, for example, for creating, increasing the level of, or dissipating a vacuum within vacuum chamber 406. Piston 420 can, but need not, include an opening (see, e.g., FIG. 5E) therein for allowing fluid communication between vacuum chamber 406 and an atmosphere surrounding vacuum chamber 406. Vacuum assembly 402 can include one or more springs, such as spring 424, for biasing piston 420 in one or more directions, for example, toward end 414 of vacuum body 410. Vacuum assembly 402 can be fluidicly coupled to vacuum chamber 406, for example, by conduit 426, which can be any conduit, such as a pipe, tube or other conduit, for routing fluid. Therefore, vacuum chamber 406 can include conduit 426 and at least a portion of vacuum body 410.

The embodiment shown in FIG. 10, which is but one of many, can generally operate or function similarly to one or more other embodiments described herein, such as to create or release a vacuum, in whole or in part, in vacuum chamber 406. For example, vacuum assembly 402 can create at least a portion of a vacuum in vacuum chamber 406 and lancing assembly 404 can lance a surface before, during, or after the vacuum exists. Vacuum assembly 402 can, but need not, create or dissipate a vacuum in portions, such as segments or stages, for example, by movement of piston 420 in one or more directions. Vacuum assembly 402 can cooperate with lancing assembly 404 to form a vacuum, in whole or in part, for example, in an embodiment, which is but one of many, wherein lancing assembly 404 includes a vacuum mechanism or can otherwise be able to create at least a portion of a vacuum independent of vacuum assembly 402. Penetration of a surface can occur at any time during lancing, such as at a predetermined time during vacuum creation, as required by a particular application.

Other and further embodiments utilizing one or more aspects of the invention described above can be devised without departing from the spirit of Applicant's invention. Further, the various methods and embodiments of the catamaran system can be included in combination with each other to produce variations of the disclosed methods and embodiments. Discussion of singular elements can include plural elements and vice-versa. References to at least one item followed by a reference to the item may include one or more items. Also, various aspects of the embodiments could be used in conjunction with each other to accomplish the understood goals of the disclosure. Unless the context requires otherwise, the word "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The invention has been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicant, but rather, in conformity with the patent laws, Applicant intends to fully protect all such modifications and improvements that come within the scope or range of equivalent of the following claims.

What is claimed is:

1. A lancing system for blood extraction, comprising:
   a tubular body having a central longitudinal axis, a lancing end and a longitudinally opposite second end, the lancing end having a first opening adapted to allow at least a portion of a lance to pass there through;
   a lancing shaft having a lance coupling end configured to couple with a lance and a longitudinally opposite actuating end, the lancing shaft being slideably coupled relative to the body with the actuating end disposed within the body;
   a stop disposed longitudinally between the lance coupling end and the actuating end of the lancing shaft, the lancing shaft being slideably coupled relative to the stop;
   a first lancing spring disposed at least partially between the stop and the lance coupling end of the lancing shaft;
   a second lancing spring disposed at least partially between the stop and the actuating end of the lancing shaft;
   a main shaft having an actuating end and a longitudinally opposite second end, wherein the main shaft is slideably coupled relative to the body and wherein the actuating end of the main shaft is disposed inside the body;
   a piston coupled to the main shaft and disposed within the body;
   a vacuum chamber formed at least partially between the piston and the first opening;
   a second opening that allows fluid communication between the vacuum chamber and an atmosphere surrounding the vacuum chamber;
   a vacuum spring coupled to the body and configured to bias the piston toward the second end of the body and away from the actuating end of the lancing shaft; and
   a shaft coupler having at least two separable portions that, when coupled, removably couple the actuating end of the lancing shaft and the actuating end of the main shaft to one another, wherein a first portion of the at least two separable portions is coupled to the actuating end of the lancing shaft and a second portion of the at least two separable portions is coupled to the actuating end of the main shaft.

2. The lancing system of claim 1, further comprising a vacuum release indicator adapted to indicate whether a vacuum is present in the system.

3. The lancing system of claim 1, further comprising a lance coupled to the lance coupling end of the lancing shaft.

4. The lancing system of claim 1, wherein the piston is adapted to form a vacuum in the vacuum chamber at a vacuum generation rate, and wherein the second opening is adapted to allow air to flow into the vacuum chamber from the atmosphere at a vacuum dissipation rate that is less than the vacuum generation rate.

5. The lancing system of claim 1, wherein the shaft coupler further comprises a coupling force between the first and second portions that exceeds a force of the first lancing spring.

6. The lancing system of claim 1, wherein the vacuum spring is adapted to move the actuating end of the lancing shaft and the actuating end of the main shaft toward the second end of the body until the stop prevents further movement of the lancing shaft thereby overcoming a coupling force between the first and second portions of the shaft coupler.

7. The lancing system of claim 6, wherein the first lancing spring is adapted to move the actuating end of the lancing shaft in a direction longitudinally opposite from the actuating end of the main shaft after the coupling force is overcome.

8. A method of extracting blood with a lancing system including a tubular body having a central longitudinal axis, a lancing end and a longitudinally opposite second end, the lancing end having a first opening adapted to allow at least a portion of a lance to pass there through, a lancing shaft having a lance coupling end configured to couple with a lance and a longitudinally opposite actuating end, the lancing shaft being slideably coupled relative to the body with the actuating end disposed within the body, a lance coupled to the lance coupling end of the lancing shaft, a stop disposed longitudinally between the lance coupling end and the actuating end of the lancing shaft, the lancing shaft being slideably coupled relative to the stop, a first lancing spring disposed at least partially between the stop and the lance coupling end of the lancing shaft, a second lancing spring disposed at least partially between the stop and the actuating end of the lancing shaft, a main shaft having an actuating end and a longitudinally opposite second end, wherein the main shaft is slideably coupled relative to the body and wherein the actuating end of the main shaft is disposed inside the body, a piston coupled to the main shaft and disposed within the body, a vacuum chamber formed at least partially between the piston and the first opening, a second opening that allows fluid communication between the vacuum chamber and an atmosphere surrounding the vacuum chamber, a vacuum spring coupled to the body and configured to bias the piston toward the second end of the body and away from the actuating end of the lancing shaft, and a shaft coupler having at least two separable portions that, when coupled, removably couple the actuating end of the lancing shaft and the actuating end of the main shaft to one another, wherein a first portion of the at least two separable portions is coupled to the actuating end of the lancing shaft and a second portion of the at least two separable portions is coupled to the actuating end of the main shaft, the method comprising:

cocking the lancing system by moving the actuating end of the main shaft, energizing the vacuum spring, and coupling the at least two separable portions of the shaft coupler together;

coupling the first opening to a surface for blood extraction and forming at least a partial seal with the surface;

deenergizing the vacuum spring;

moving the at least two separable portions of the shaft coupler in a first direction toward the second end of the body;

stopping the first portion of the shaft coupler;

uncoupling the at least two separable portions of the shaft coupler;

moving the first portion of the shaft coupler in a second direction longitudinally opposite from the first direction;

creating a vacuum in the vacuum chamber; and lancing the surface while the surface is subjected to the vacuum.

9. The method of claim 8, further comprising:

creating a first portion of the vacuum prior to lancing the surface; and creating a remaining portion of the vacuum after the surface has been lanced.

10. The method of claim 8, further comprising:

creating the vacuum at a vacuum generation rate; and dissipating the vacuum by allowing air to flow into the vacuum chamber through the second opening at a vacuum dissipation rate;

wherein the vacuum dissipation rate is less than the vacuum generation rate.

11. The method of claim 10, further comprising creating the vacuum and dissipating the vacuum simultaneously.

12. The method of claim 8, further comprising:

moving the second portion of the shaft coupler in the first direction while the first portion of the shaft coupler is moving in the second direction.

13. A lancing system for blood extraction, comprising:

a tubular body having a central longitudinal axis, a lancing end and a longitudinally opposite second end;

a lancing shaft having a lance coupling end configured to couple with a lance and a longitudinally opposite actuating end, the lancing shaft being slideably coupled relative to the body with the actuating end disposed within the body;

a stop disposed longitudinally between the lance coupling end and the actuating end of the lancing shaft, the lancing shaft being slideably coupled relative to the stop;

a first lancing spring disposed at least partially between the stop and the lance coupling end of the lancing shaft;

a second lancing spring disposed at least partially between the stop and the actuating end of the lancing shaft;

a main shaft having an actuating end and a longitudinally opposite second end, wherein the main shaft is slideably coupled relative to the body and wherein the actuating end of the main shaft is disposed inside the body; and a shaft coupler having at least two separable portions that, when coupled, removably couple the actuating end of the lancing shaft and the actuating end of the main shaft to one another, wherein a first portion of the at least two separable portions is coupled to the actuating end of the lancing shaft and a second portion of the at least two separable portions is coupled to the actuating end of the main shaft; and a main spring configured to bias the main shaft, wherein the main spring is adapted to move the actuating end of the lancing shaft and the actuating end of the main shaft toward the second end of the body until the stop prevents further movement of the lancing shaft thereby overcoming a coupling force between the first and second portions of the shaft coupler.

14. The lancing system of claim 13, further comprising a lancing depth controller coupled to the lancing end of the body.

15. The lancing system of claim 13, further comprising a lance coupled to the lance coupling end of the lancing shaft.

16. The lancing system of claim 13, further comprising a vacuum release indicator adapted to indicate whether a vacuum is present in the system.

17. The lancing system of claim 13, wherein the shaft coupler further comprises a coupling force between the first and second portions that exceeds a force of the first lancing spring.

18. The lancing system of claim 13, wherein the first lancing spring is adapted to move the actuating end of the lancing shaft in a direction longitudinally opposite from the actuating end of the main shaft after the coupling force is overcome.

19. The lancing system of claim 13, wherein at least one of the at least two separable portions of the shaft coupler is selected from the group consisting of a magnet, magnetic material, hook material, loop material, a ball, a joint adapted to removably couple with a ball, and a combination thereof.

\* \* \* \* \*